United States Patent [19]

Poss et al.

[11] Patent Number: 5,399,725

[45] Date of Patent: Mar. 21, 1995

[54] 7-OXABICYCLOHEPTANE CARBOXYLIC ACID PROSTAGLANDIN ANALOG INTERMEDIATES USEFUL IN THE PREPARATION OF ANTI-THROMBOTIC AND ANTI-VASOSPASTIC COMPOUNDS AND METHOD FOR PREPARING SAME

[75] Inventors: Michael A. Poss, Lawrenceville; Paul D. Pansegrau; Shaopeng Wang, both of E. Windsor; John K. Thottathil, Robbinsville; Janak Singh, Lawrenceville; Richard H. Mueller, Ringoes, all of N.J.

[73] Assignee: Bristol-Myers Squibb Co., Princeton, N.J.

[21] Appl. No.: 226,091

[22] Filed: Apr. 20, 1994

Related U.S. Application Data

[63] Continuation-in-part of Ser. No. 67,886, May 27, 1993, abandoned.

[51] Int. Cl.$^6$ ............... C07D 307/10; C07D 317/12
[52] U.S. Cl. .................................................. 549/448
[58] Field of Search ........................................ 549/448

[56] References Cited

U.S. PATENT DOCUMENTS 5,175,304 12/1992 Sheppard et al. ................... 548/431

OTHER PUBLICATIONS

Anderson, W. K. et al "A Retro-Diels-Alder Synthesis of 3-Pyrrolines", J. Org. Chem., 1985, 50, 5423–5424.

Walter, C. J. et al, "exo-Selective Acceleration of an Intermolecular diels-Alder Reaction by a Trimeric Porphyrin Host", J. Chem. Soc., Chem. Commun., 1993, 458–460.

Arai, Y. et al, "Powerful Dienophiles for Asymmetric Diels-Alder Reaction: α-(2-exo-Hydroxy-10-bornylsulfinyl)maleimides", J. Org. Chem. 1991, 56, 1983–1985.

Hartman, G. D. et al, "Iminium Ion Mediated Cyclizations of 4-Aryl-1,4-dihydropyridines, Bridging with Acetals, Carbonyls, and Thiocarbonyls", J. Org. Chem. 1985, vol. 50, pp. 2423–2427.

Miller, S. A. et al, "Highly Selective Formation of Cis-Substituted Hydroxylactams via Auxiliary-Controlled Reduction of Imides", J. Org. Chem., 1989, vol. 54, pp. 2502–2504.

Mukaiyama, T. et al, "An Asymmetric Synthesis of Bicyclic Lactones and its Application to the Asymmetric Synthesis of (1R,3S)-cis-Chrysanthemic Acid", Chemistry Letters, 1983, pp. 385–388.

Organic Syntheses Collective vol. 4, 1951, pp. 327–329, 2,3-Dimethoxycinnamic Acid, Koo et al.

Kwart, H. et al, "Isomerism and Adduct stability in the Diels-Alder Reaction, I. The Adducts of Furan and Maleimide", J. Am. Chem. Soc., vol. 74, 1951, pp. 3094–3097.

Yates, P. "Acceleration of the Diels-Alder Reaction by Aluminum Chloride", J. Am. Chem. Soc., vol. 82, Aug. 20, 1960, pp. 4436–4437.

March, Advanced Organic Chemistry, 2nd Edition, pp. 836–841, 1977.

*Primary Examiner*—Mary C. Lee
*Assistant Examiner*—Joseph McKane
*Attorney, Agent, or Firm*—Burton Rodney

[57] ABSTRACT

A method is provided for preparing carboxylic acid intermediates of the structure

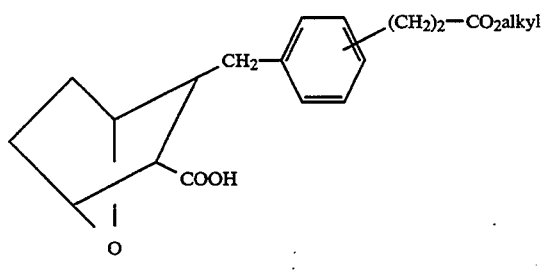

wherein an aldehyde of the structure (Abstract continued on next page.)

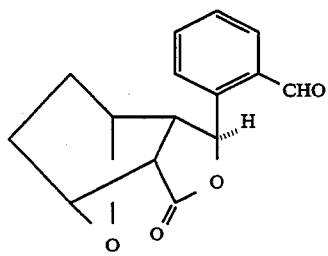
is prepared and subjected to a Horner-Emmons reaction to form the ester of the structure
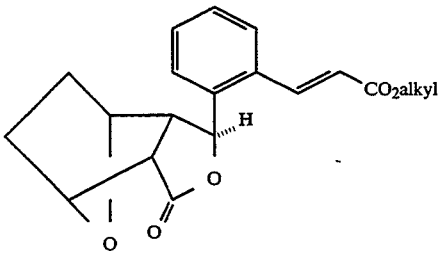
and the ester is hydrogenated to the carboxylic acid which may be used in making the final anti-thrombotic—anti-vasospastic compounds.
4 Claims, No Drawings

7-OXABICYCLOHEPTANE CARBOXYLIC ACID PROSTAGLANDIN ANALOG INTERMEDIATES USEFUL IN THE PREPARATION OF ANTI-THROMBOTIC AND ANTI-VASOSPASTIC COMPOUNDS AND METHOD FOR PREPARING SAME

REFERENCE TO OTHER APPLICATIONS

This is a continuation-in-part of U.S. patent application Ser. No. 067,886 filed May 27, 1993, now abandoned.

FIELD OF THE INVENTION

The present invention relates to novel 7-oxabicycloheptane carboxylic acid prostaglandin analog intermediates which may be used to prepare a final anti-thrombotic—anti-vasospastic product, and to methods for preparing same.

BACKGROUND OF THE INVENTION

U.S. Pat. No. 5,100,889 to Misra et al discloses 7-oxabicycloheptyl substituted heterocyclic amide prostaglandin analogs which are thromboxane $A_2$ ($TXA_2$) receptor antagonists or combined thromboxane $A_2$ receptor antagonist/thromboxane synthetase inhibitors useful, for example, in the treatment of thrombotic and/or vasospastic diseases, and have good duration of action. Examples of compounds disclosed in Misra et al have the structural formula I

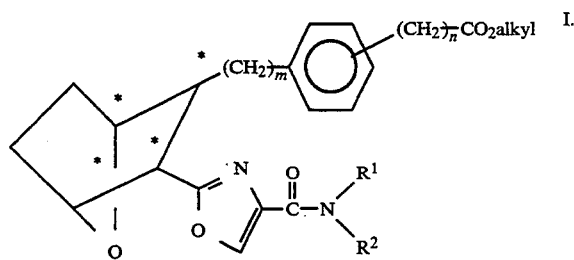

and including all stereoisomers thereof, wherein
m is 1, 2 or 3; n is 0, 1, 2, 3 or 4;
$R^1$ is hydrogen, lower alkyl, aralkyl, aryl, cycloalkyl, cycloalkylalkyl, or amide

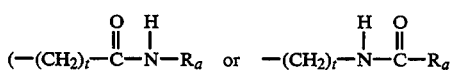

wherein t is 1 to 12 and $R_a$ is lower alkyl, aryl, cycloalkyl, or cycloalkylalkyl);
$R^2$ is hydrogen, lower alkyl, aryl, or aralkyl; or $R^1$ and $R^2$ together with the nitrogen to which they are linked may form a 5- to 8- membered ring.

Misra et al disclose that these compounds may be prepared by transmetallating bromophenylalkyl B

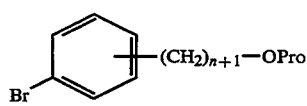

by treatment with $t\text{-}C_4H_9Li$ or $n\text{-}C_4H_9Li$ or subjecting B to a Grignard reaction by treatment with Mg, and then condensing with the perhydro benzopyran-3-ol derivative or the perhydro benzofuran-1-ol derivative C

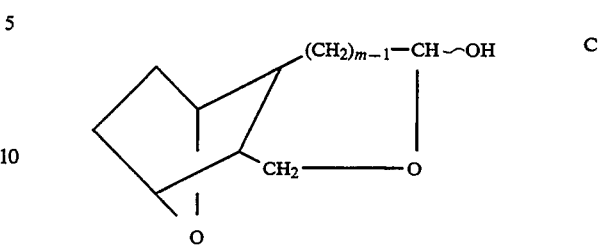

to form the condensed 7-oxabicycloheptane alcohol compound of the structure Z

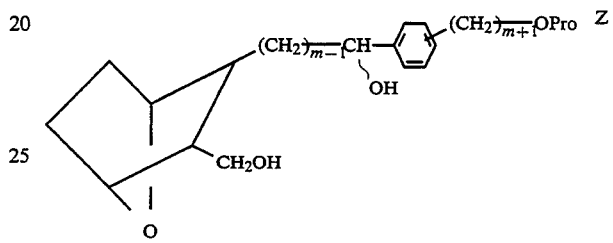

and then subjecting the condensed compound to hydrogenolysis to form the following alcohol

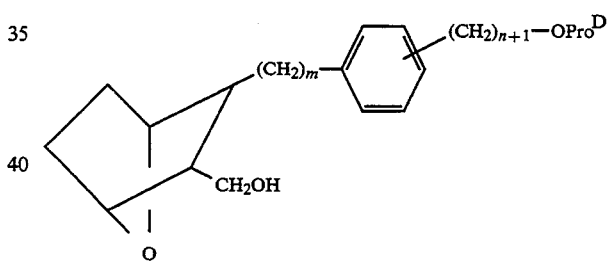

Where Pro is thexyldimethylsilyl or t-butyldimethylsilyl, the alcohol is acetylated and the silyl protecting group of the so-formed acetate is removed to form the following acetate:

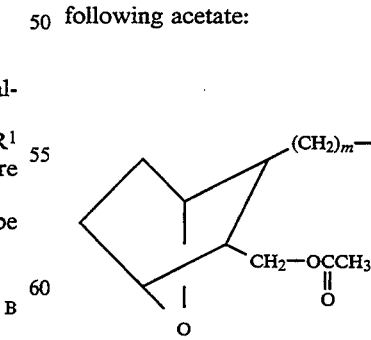

which is treated with a protecting compound and the acetate is removed by treatment with aqueous hydroxide or excess methyllithium to form the following alcohol:

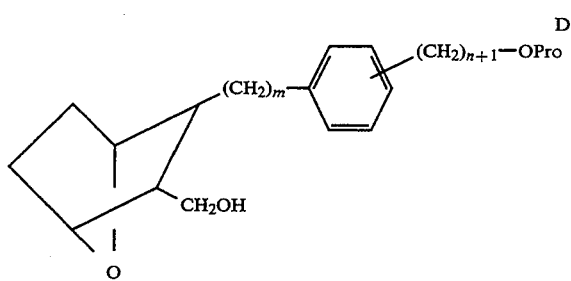

(where Pro is t-butyldiphenylsilyl). The protected alcohol is subjected to a Jones oxidation to form the following acid:

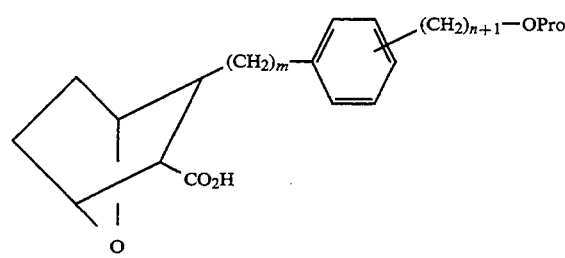

The so-formed carboxylic acid intermediate is then employed to make the final compound.

In a more preferred procedure, Misra et al disclose protecting the alcohol function of alcohol Z to form the protected alcohol

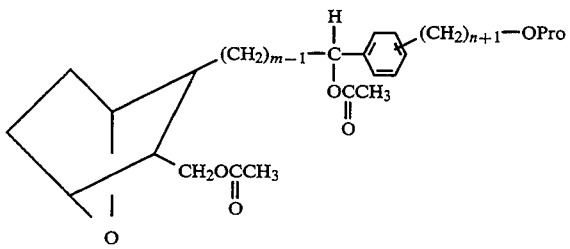

subjecting the protected alcohol to a Jones oxidation and esterification to form the ester

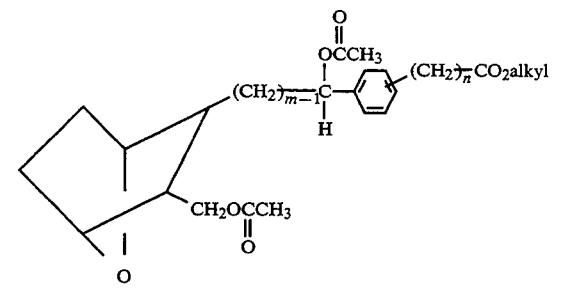

which is made to undergo hydrogenolysis and subsequent removal of the acetate protecting group by transesterification to afford the alcohol

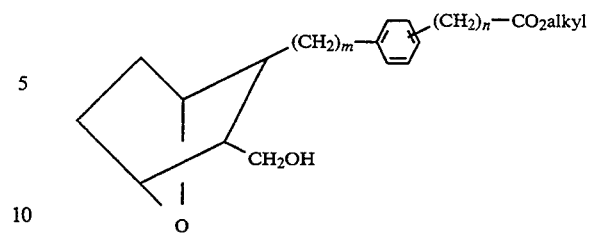

which is subjected to a Jones oxidation to form the carboxylic acid intermediate II

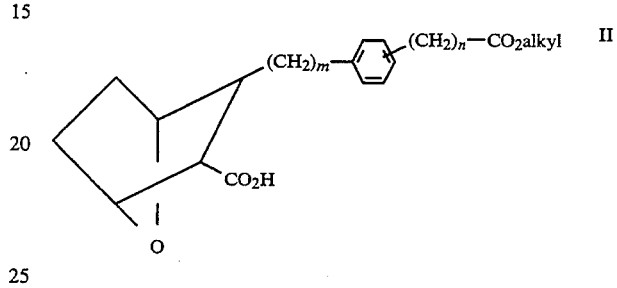

In an alternative procedure where n is 1, the above carboxylic acid intermediate II is formed by treating D' with acetic anhydride and removing the protecting group to form the acetate alcohol

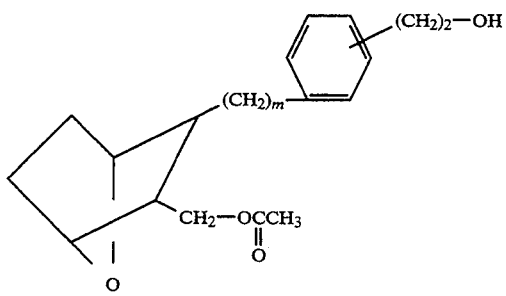

which is made to undergo a Dess-Martin oxidation to form the aldehyde

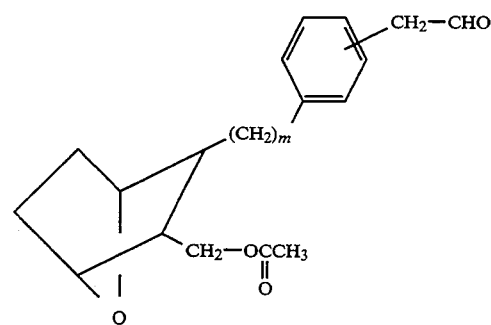

The above aldehyde is oxidized and esterified to the corresponding acetate ester, deprotected, and subjected to a Jones oxidation to form carboxylic acid II where n is 1.

Description of the Invention

In accordance with the present invention, methods are provided for preparing intermediates for use in the preparation of 7-oxabicycloheptyl substituted oxazole amide prostaglandin analogs as described hereinafter which are useful as anti-thrombotic and anti-vasospastic compounds.

The methods of the invention are outlined in Reaction Schemes 1 to 6 set out hereinafter.

Reaction Scheme 1
Preparation of Carboxylic Acid Intermediate IIA

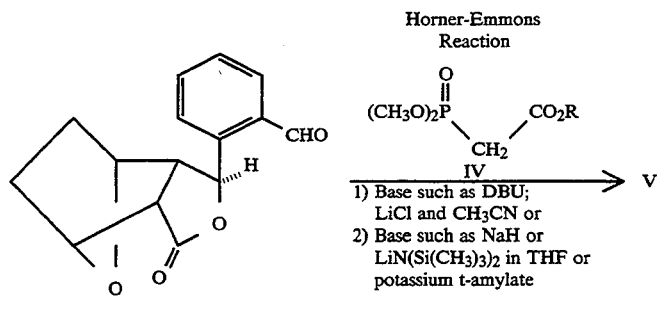

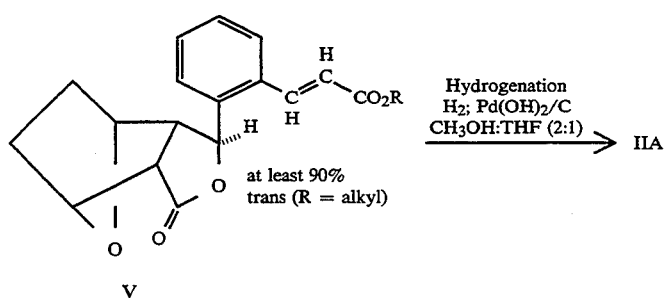

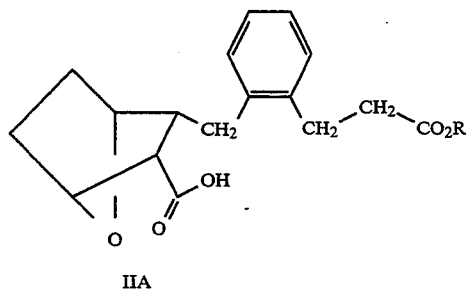

Reaction Scheme 2
Alternate Preparation of Carboxylic Acid Intermediate IIA

Knoevenagel Reaction
Malonic Acid
Pyridine
Piperidine
III 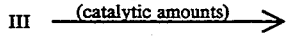  (catalytic amounts)

-continued
Reaction Scheme 2

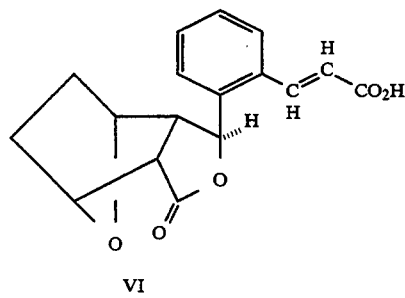

VI 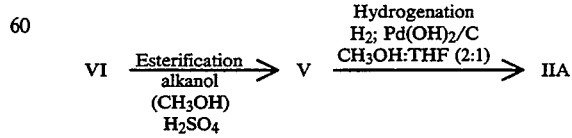 V  Hydrogenation H₂; Pd(OH)₂/C CH₃OH:THF (2:1) → IIA

Reaction Scheme 3
Preparation of Starting Aldehyde III

-continued
Reaction Scheme 3
Imide formation

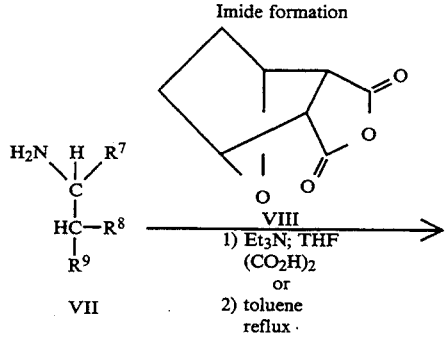

VII
1) Et₃N; THF
(CO₂H)₂
or
2) toluene
reflux

VIII

-continued
Reaction Scheme 3

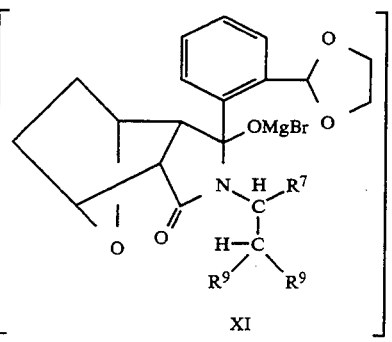

XI

[XI] $\xrightarrow{\text{Reduction} \atop \text{NaBH}_4 \atop \text{Ethanol}}$

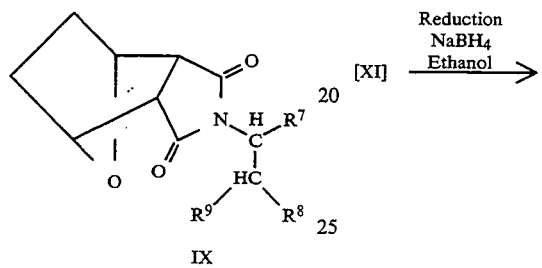

IX

IX $\xrightarrow{\text{Grignard Reaction} \atop \text{EtMgCl (present where} \atop R^9 \text{ is OH); THF}}$

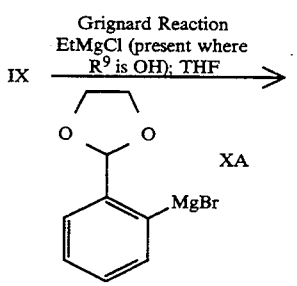

XA

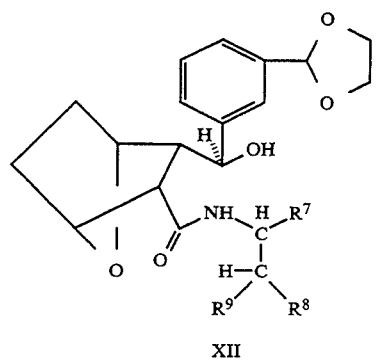

XII

XII $\xrightarrow{\begin{array}{l}\text{1) Toluene (Lactonization)}\\ \text{2) 1N NaOH:EtOH (4:1)}\\ \text{3) Wash EtOAc}\\ \text{4) THF; 10\% HCl to pH<2}\end{array}}$

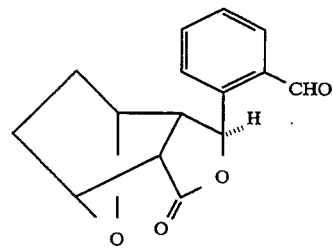

III

Reaction Scheme 4

Preparation of Final Product
Starting with Carboxylic Acid Intermediate IIA

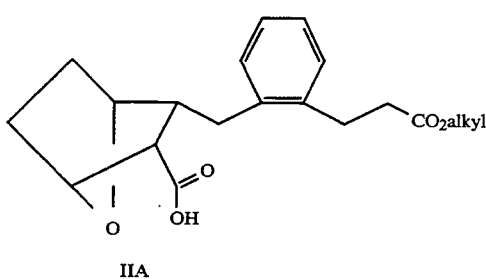

IIA

Coupling Reaction
1) oxalyl chloride,
   toluene, DMF (cat.)
2) CH₃C(O)C₂H₅
   Aq. NaHCO₃

$\longrightarrow$ XIV

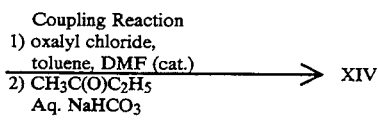

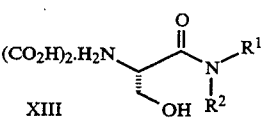

XIII

-continued
Reaction Scheme 4
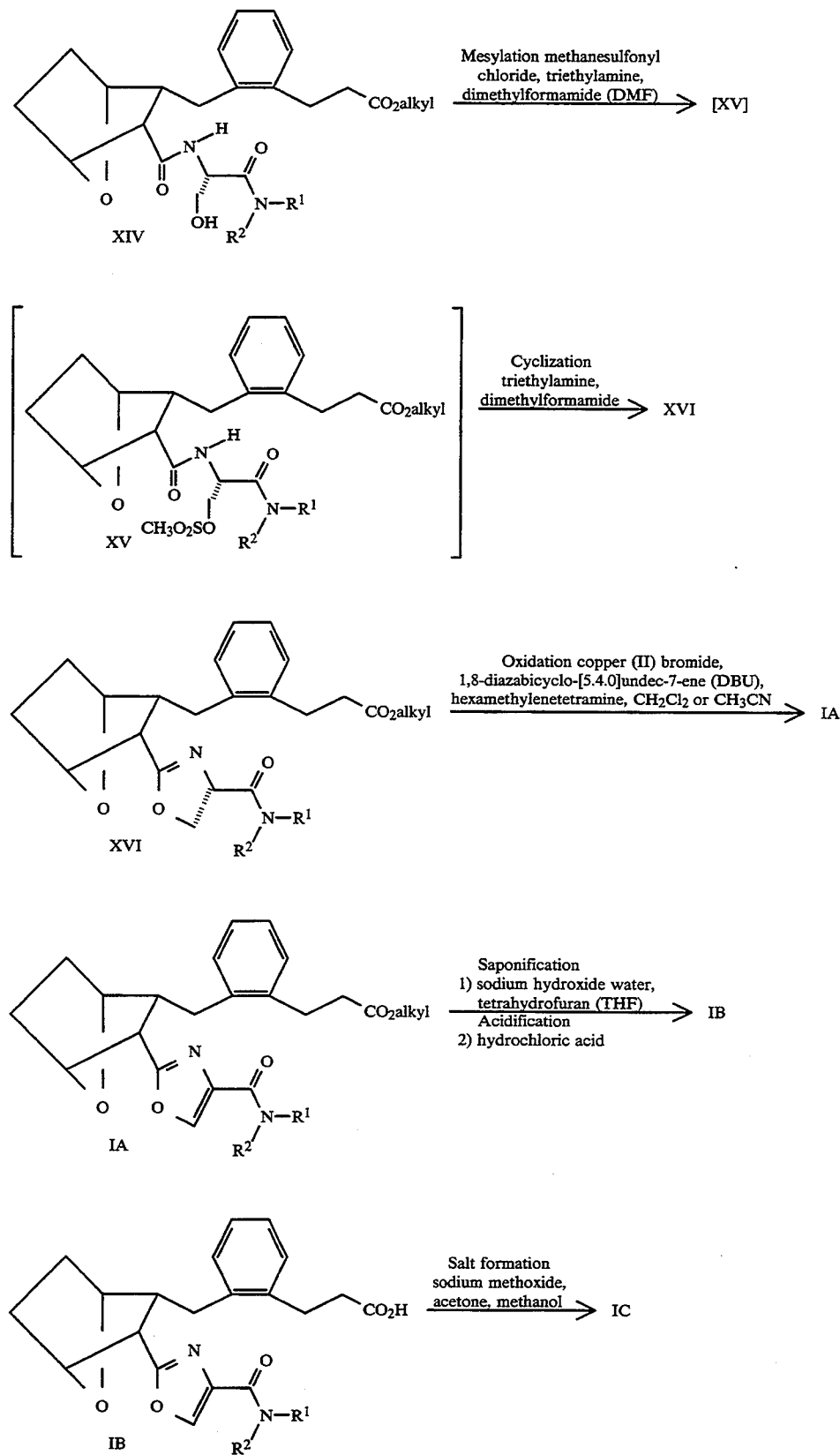

-continued
Reaction Scheme 4

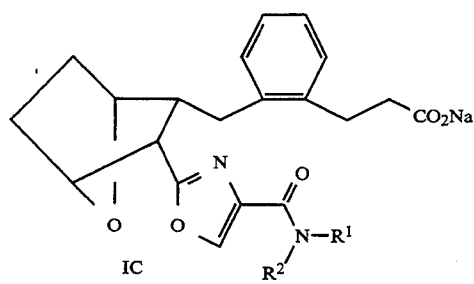

Reaction Scheme 5
Preparation of Starting Compound XIII

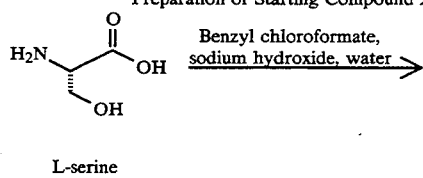

L-serine

Benzyl chloroformate,
sodium hydroxide, water →

Alternative Preparation of Intermediate Chiral Imide IX where $R^7 \neq H$

Scheme 6A

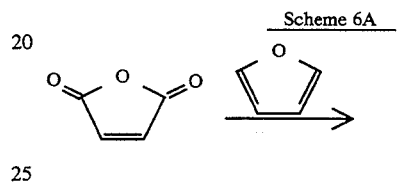

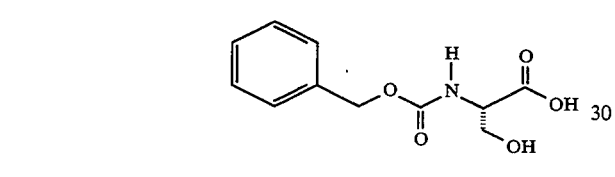

carbobenzyloxy-L-serine

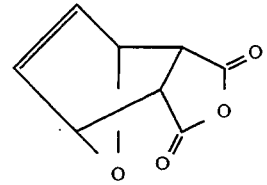

VIIa

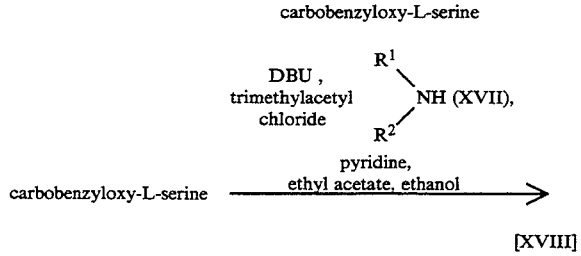

carbobenzyloxy-L-serine

DBU,
trimethylacetyl
chloride pyridine,
ethyl acetate, ethanol
→

[XVIII]

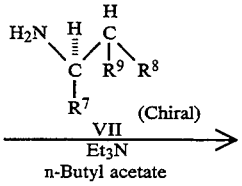

VIIa —VII (Chiral)→
Et₃N
n-Butyl acetate

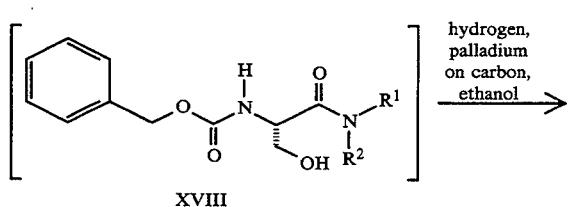

XVIII hydrogen,
palladium
on carbon,
ethanol
→

[XIX]

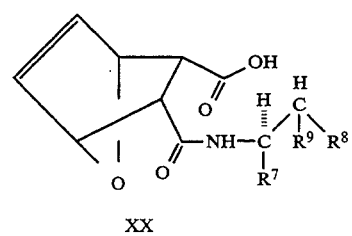

XX (mixture of diastereromers)

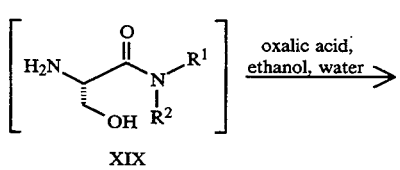

XIX oxalic acid,
ethanol, water →

XX 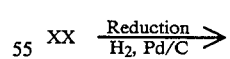 →

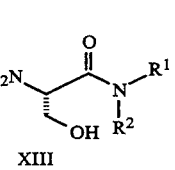

XIII

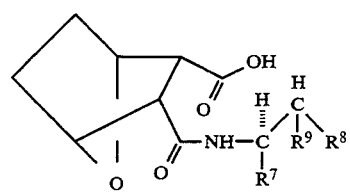

XXII (mixture of diastereromers)

Reaction Scheme 6

-continued
Scheme 6A
XXII →(Cyclization)→
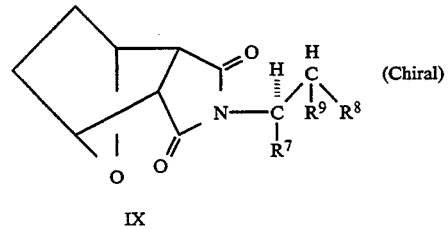
IX
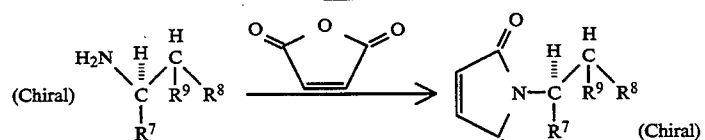
Scheme 6B
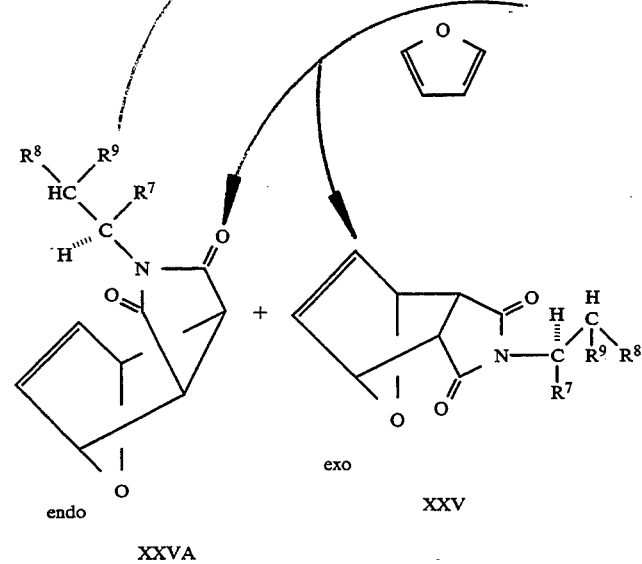
endo XXVA
exo XXV
XXV →(H₂, Pd—C / EtOAc)→
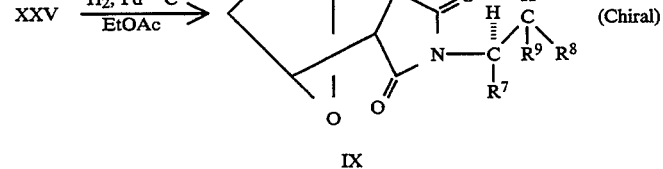
IX
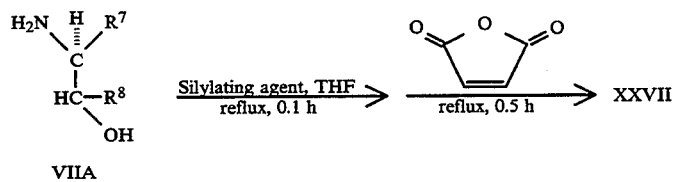
Scheme 6C
VIIA →(Silylating agent, THF / reflux, 0.1 h)→ →(reflux, 0.5 h)→ XXVII

Scheme 6C
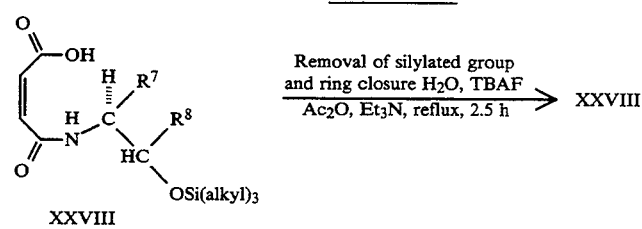
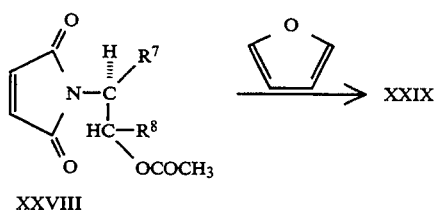
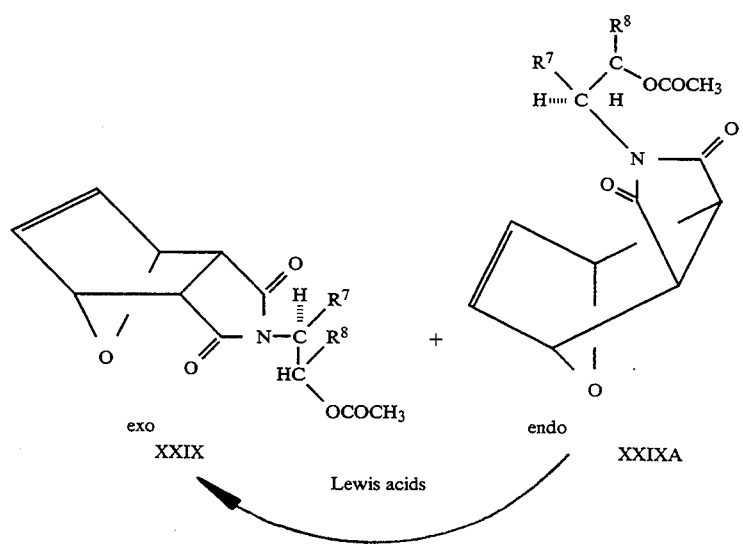
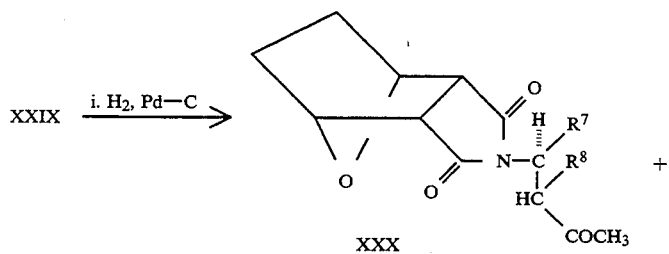
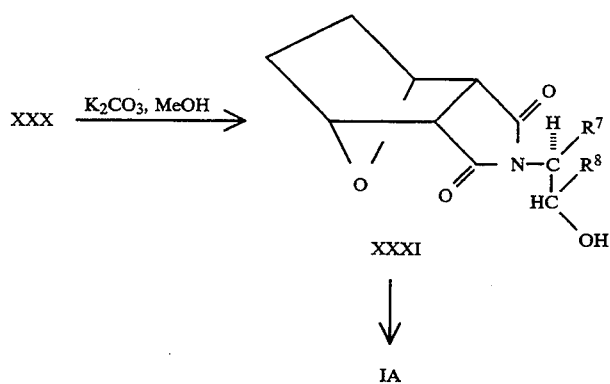

Scheme 6C

IB

IC

Referring to the above Reaction Schemes, one aspect of the present invention includes a method for preparing carboxylic acid starting material IIA

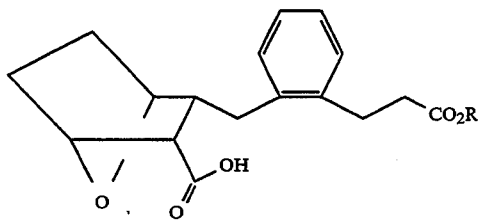

wherein R is lower alkyl preferably methyl or ethyl. As shown in Reacton Scheme 1, in accordance with the present invention, carboxylic acid IIA is prepared from starting aldehyde III (which is a novel compound in accordance with the invention) and is preferably in substantially enantiomerically pure form, which is made to undergo a Horner-Emmons reaction wherein aldehyde III is treated with a phosphonic diester compound IV in the presence of a base such as 1,8-diazabicyclo-[5.4.0]-undec-7-ene (DBU), or 1,5-diazabicyclo-[4.3.0]non-5-ene (DBN), or Hunig's base (diisopropylethylamine), preferably DBU, and an inert organic solvent such as acetonitrile, tetrahydrofuran (THF), dimethoxyethane or toluene, preferably, acetonitrile, and an alkali metal salt such as lithium chloride, lithium bromide, or an alkaline earth metal salt such as MgBr$_2$, or magnesium methoxide, to form the ester V wherein R is lower alkyl such as methyl or ethyl (which is a novel compound in accordance with the present invention). As shown in Scheme 1, the ester V will be primarily in the form of the trans isomer.

Alternatively, the Horner-Emmons reaction may be carried out by substituting for DBU, as a base, an alkali metal hydride such as sodium hydride, or lithium bis(-trimethylsilyl)amide, or potassium t-amylate, in an inert organic solvent such as tetrahydrofuran, toluene or dimethoxyethane.

In another variation on Scheme 1, the aldehyde III may be homologated to form ester V by treating III with a magnesium salt of a monoalkyl malonate of the structure p

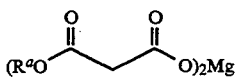

IVA wherein R$^a$ is a lower alkyl, such as methyl or ethyl, in the presence of THF or other etheral solvent such as diethyl ether.

The ester V (primarily in the form of the trans isomer) will be subjected to a hydrogenation wherein ester V is treated with hydrogen in the presence of a hydrogenation catalyst such as Pd(OH)$_2$/C or Pd/C, and in the presence of an alcohol solvent such as methanol or ethanol, and an inert organic solvent such as THF, ethyl acetate or dioxane, to form carboxylic acid IIA.

In an alternative embodiment as shown in Reaction Scheme 2, carboxylic acid intermediate IIA is formed by subjecting aldehyde III to a Knoevenagel reaction where III is treated with malonic acid in the presence of a base-solvent such as pyridine, 2,6-lutidine or collidine, and a catalytic amount of piperidine, to form acid VI (which is a novel compound in accordance with the present invention). Acid VI may then be esterified, for example, by reaction with an alkanol, such as methanol or ethanol, in the presence of a strong acid catalyst such as sulfuric acid, p-toluenesulfonic acid or camphorsulfonic acid, to form the ester V. Ester V may then be hydrogenated as described above with respect to Reaction Sequence 1, to form carboxylic acid intermediate IIA.

The starting aldehyde III may be prepared, in accordance with the present invention, as shown in Reaction Scheme 3 starting with amine VII

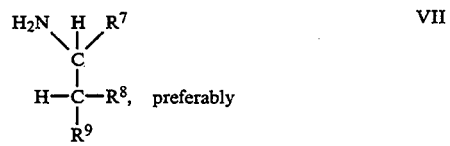

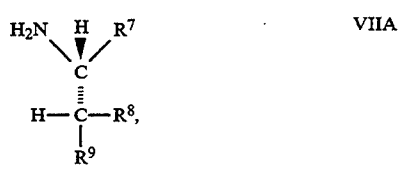

wherein R$^7$ is aryl or lower alkyl, preferably phenyl,
R$^8$ is H, aryl or lower alkyl, preferably H,
R$^9$ is H, OH or lower alkyl, preferably OH or H.

However where R$^9$ is OH, amine VII will preferably have the structure

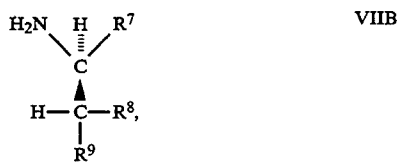

Amine VII is made to undergo imide formation by dehydration by reacting VII with anhydride VIII in the presence of a weak organic base such as triethylamine, diisopropylethylamine or N-ethylpiperidine, an inert organic solvent such as THF, toluene or benzene and an acid such as oxalic acid, malonic acid or p-toluenesulfonic acid, to form imide IX which is a novel intermediate.

Alternatively, imide IX may be formed by reacting VII with anhydride VIII in the presence of an aromatic solvent such as toluene, benzene or xylene, preferably at reflux with azeotropic removal of water.

Imide IX is then subjected to an addition reaction by treating IX with a metallated aryl compound of the structure

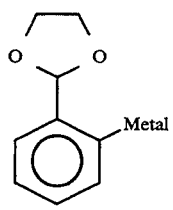

X wherein Metal is MgBr or Li. Where Metal is MgBr, such Grignard reagent XA is prepared by dissolving the halide

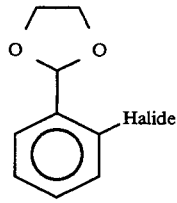

(wherein halide refers to Br or I), in an inert organic solvent, such as THF, dioxane, toluene or t-butylmethyl ether, and mixing the so-formed solution with magnesium to give the aryl Grignard reagent XA.

A cooled solution of imide IX in an inert organic solvent such as THF, t-butylmethyl ether, toluene or dioxane, is mixed with a solution of an alkyl (or aryl) magnesium halide such as ethylmagnesium chloride, ethylmagnesium bromide or phenylmagnesium chloride (used only if $R^9$ is OH) in the same solvent used for imide IX, followed by the Grignard reagent XA, to form intermediate XI which is reduced, for example, by reaction with a reducing agent such as sodium borohydride, lithium borohydride or zinc borohydride, in the presence of an alcohol solvent such as ethanol or methanol, to form amide XII.

Where the metallated aryl compound X to be employed is the aryl lithium derivative XB and $R_9$=OH, imide IX may be first treated with an alkyl lithium compound ($R^aLi$ where $R^a$ is lower alkyl) such as methyllithium, ethyllithium or butyllithium, and then with the aryllithium derivative XB

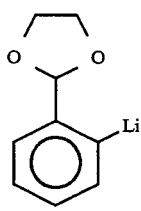

XB in the presence of an inert organic solvent such as THF, toluene, tert-butylmethyl ether or diethyl ether. The resulting intermediate XIA (same as XI except MgBr is replaced with Li) is reduced as described for XI to form amide XII.

Amide XII is made to undergo lactonization by dissolving XII in toluene and heating to form the lactone XIIA (which is a novel intermediate)

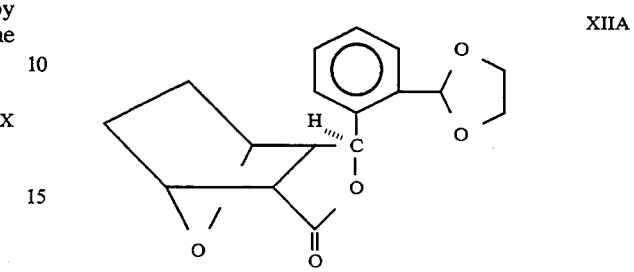

XIIA which is treated with water and a base such as NaOH, KOH, LiOH, $Mg(OH)_2$ or $Ca(OH)_2$ in the presence of an alcohol solvent such as ethanol or methanol, to form the salt XIIB (which is a novel intermediate)

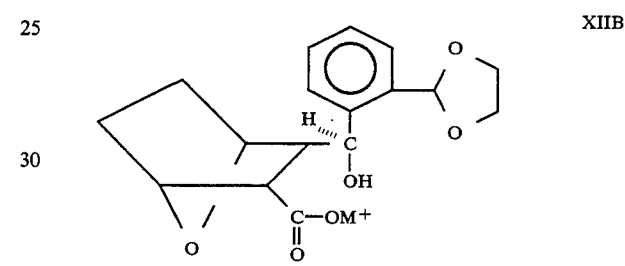

XIIB where $M^+$ is a metal ion such as $Na^+$, $K^+$ and the like.

XII may be treated with NaOH directly to form salt XIIB.

Salt XIIB is then treated with strong acid such as hydrochloric acid, sulfuric acid, or nitric acid in the presence of an inert organic solvent, such as THF, isopropanol or dioxane, to form starting aldehyde III as a single enantiomer as shown.

In a further aspect of the present invention, as seen in Reaction Scheme 4, the carboxylic acid IIA intermediate is employed to prepare a thromboxane receptor antagonist IA-IC. As seen in Scheme 4, carboxylic acid IIA is subjected to a coupling reaction wherein carboxylic acid IIA in an inert solvent such as toluene, methylene chloride, or 1,2-dichloroethane is treated under an inert atmosphere with a catalytic amount of DMF. The resulting mixture is cooled below 0° C. and oxalyl chloride or other reagent for acid chloride formation such as thionyl chloride is added to form an acid chloride solution. Where thionyl chloride is to be employed, carboxylic acid IIA need not be treated with catalytic DMF.

Amide XIII (prepared as described in Scheme 5) is added to an aqueous sodium bicarbonate solution and an inert organic solvent such as methyl ethyl ketone, methylene chloride or THF is added to form a biphasic mixture which is cooled to from about 30° to about −10° C. The previously prepared acid chloride solution is added and the mixture heated to a temperature within the range of from about 40° to about 80° C. to form amide XIV.

Amide XIV is mesylated by treating a solution of amide XIV in DMF or other solvent such as methylene chloride or THF, with an organic base such as triethylamine, pyridine or 2,6-lutidine and then while maintaining the mixture below about 5° C., methanesulfonyl chloride is added to form the mesylate XV. Mesylate XV is cyclized by treating XV with triethylamine or other organic base as set out above, in the presence of DMF or other solvent as set out above to form oxazoline XVI.

Oxazoline XVI is oxidized using cupric bromide and 1,8-diazabicyclo[5.4.0]undec-7-ene (DBU) in the presence of hexamethylenetetramine and an inert organic solvent such as methylene chloride to form oxazole ester IA which is saponified by treatment with strong base such as NaOH, KOH and the like, in aqueous-organic solvent such as THF or dioxane, and then is acidified by treatment with strong acid such as HCl, sulfuric acid or trifluoroacetic acid to form oxazole acid IB. Oxazole acid IB may then be treated with alkali metal alkoxide such as sodium methoxide, sodium 2-ethan-hexanoate or sodium ethoxide, in the presence of inert organic solvent such as acetone, THF or ethyl acetate, and an alcohol such as methanol or ethanol to form oxazole salt IC.

Referring to Reaction Scheme 5, the amide XIII (used in Scheme 4) is prepared by reacting an aqueous solution of L-serine and NaOH with benzyl chloroformate to form carbobenzyloxy-L-serine which is treated with DBU under an inert atmosphere. Thereafter trimethylacetyl chloride and amine XVII are added to form amide XVIII which is deprotected by treatment with $H_2$ and Pd/C in the presence of an alcohol solvent, such as ethanol or methanol, to form amide XIX which is treated with oxalic acid or another acid such as HCl or trifluoroacetic acid in the presence of alcohol solvent such as ethanol or methanol to form amide XIII.

In the amine XVII, $R^1$ and $R^2$ are as defined in U.S. Pat. No. 5,100/889 which is incorporated herein by reference.

Thus, $R^1$ is hydrogen, lower alkyl, aralkyl, aryl, cycloalkyl, cycloalkylalkyl, or amide

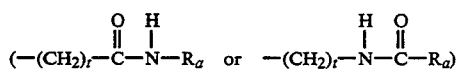

wherein t is 1 to 12 and $R_a$ is lower alkyl, aryl, cycloalkyl, or cycloalkylalkyl); and $R^2$ is hydrogen, lower alkyl, aryl, or aralkyl; or $R^1$ and $R^2$ together with the nitrogen to which they are linked may form a 5- to 8- membered ring.

$R^1$ is preferably lower alkyl such as n-pentyl, aryl such as phenyl, halophenyl such as 4-chlorophenyl, or cyclohexylalkyl, such as cyclohexylbutyl.

$R^2$ is preferably H or phenyl.

The novel intermediates of the invention have the structures

A.

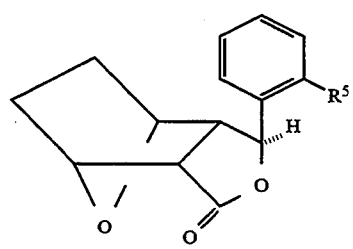

wherein $R^5$ is —CHO or —CH=CH—$CO_2R^6$ wherein $R^6$ is H or alkyl (A. will preferably be in enantiomerically pure form as shown and may be prepared in such pure form employing the procedures described herein);

B.

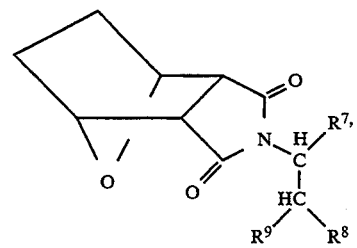

C.

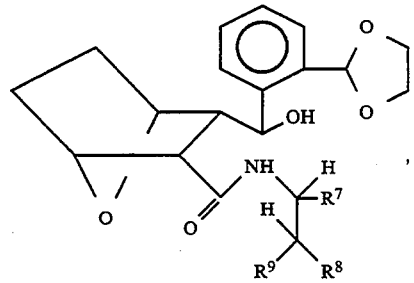

D.

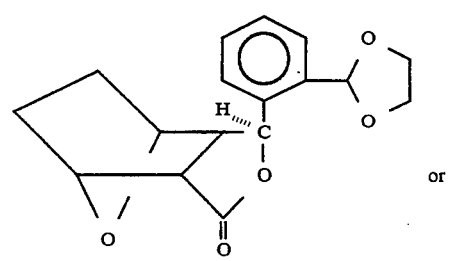

or

E.

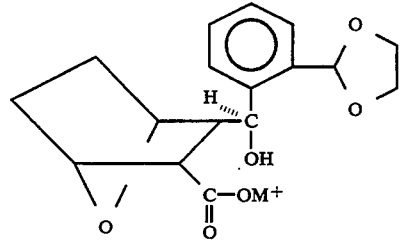

including all stereoisomers thereof, wherein
$R^7$ is aryl or lower alkyl, preferably phenyl,
$R^8$ is H, aryl or lower alkyl, preferably H and
$R^9$ is H, OH or lower alkyl, preferably OH or H.

In compound B, where $R^9$ is OH, compound B will preferably comprise the enantiomer

B'.

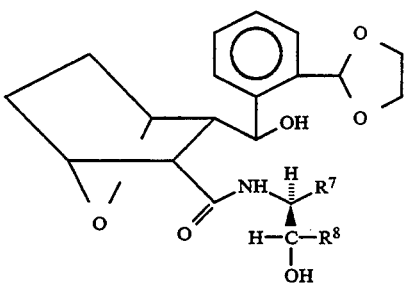

In Compound B where R⁹ is not OH, compound B will preferably comprise the enantiomer

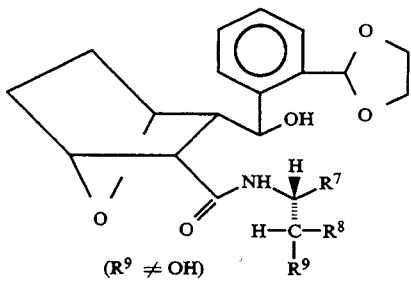

B''.

(R⁹ ≠ OH)

Detailed Description of the Invention

In carrying out the method of the invention as shown in Scheme 1 for preparing carboxylic acid IIA, the Horner-Emmons reaction is carried out in the presence of base and optionally an alkali or alkaline earth metal salt such as a lithium halide, for example, lithium chloride, lithium bromide, lithium iodide or magnesium bromide, employing a molar ratio of phosphonic acid IV: aldehyde III of within the range of from about 1:1 to about 1.5:1, preferably from about 1:1 to about 1.2:1, under an inert atmosphere such as argon or nitrogen, to form the ester V in a ratio of trans:cis isomers of within the range of from about 14:1 to about 36:1.

Where ester V is formed by homologation of aldehyde III employing the magnesium salt of a monoalkylmalonate (IVA), the magnesium salt IVA will be employed in a molar ratio to aldehyde III of within the range of from about 1:1 to about 2:1.

The so-formed ester V is then hydrogenated preferably employing Pearlman's catalyst (Pd(OH)$_2$/C) to form the carboxylic acid IIA. Other catalysts, such as palladium on carbon may be employed in carrying out the hydrogenation step.

Alternatively, as seen in Scheme 2, the aldehyde III may be subjected to a Knoevenagel reaction employing a molar ratio of malonic acid:aldehyde III of within the range of from about 6:1 to about 3:1, preferably from about 5:1 to about 4:1. The reaction is carried out at a temperature within the range of from about 60° to about 100° C. The resulting acid VI is esterified with an alkanol, preferably methanol or ethanol, employing conventional techniques to form the ester V which may be hydrogenated as described above to form carboxylic acid IIA.

The aldehyde III is prepared as shown in Scheme 3 wherein the amine VII is reacted with anhydride VIII employing a molar ratio of VII:VIII of within the range of from about 1:1 to about 1.5:1, preferably from about 1.2:1 to about 1.0:1. The reaction, including oxalic acid or other acid and base and solvent, is carried out at a temperature within the range of from about 40° to about 100° C., preferably from about 60° to about 80° C.

Where toluene is employed in place of base and oxalic acid, the reaction of VII and VIII is carried out at a temperature within the range of from about 80° to about 120° C., preferably from about 100° to about 115° C.

The resulting imide IX is then subjected to an addition reaction, such as a Grignard reaction, to ultimately form aldehyde III of desired optical purity.

In carrying out the Grignard reaction, the aryl Grignard reagent XA is prepared by treating a solution of 2-(2-halophenyl)-1,3-dioxolane (where halo is Br or I) in THF or other inert organic solvent such as dioxane or t-butylmethyl ether, with magnesium, preferably in the form of Mg turnings, employing a molar ratio of Mg:2-(2-bromophenyl)-1,3-dioxolane of within the range of from about 2:1 to about 1.0:1, preferably from about 1.1:1 to about 1.5:1.

If imide IX has R$_9$=OH, then imide IX is first treated with an alkyl- or aryl- magnesium halide (e.g. Cl⁻, Br⁻ or I⁻), preferably ethyl magnesium chloride, employing a molar ratio of imide IX to ethylmagnesium halide within the range of from about 1:1.1 to 1:1. The so-formed aryl Grignard reagent XA is then mixed with the reaction solution employing a molar ratio of imide IX to aryl Grignard reagent XA of within the range of from about 1:4 to about 1:1, preferably from about 1:1.2 to about 1:2.5. If imide IX has R$_9$≠OH then the so-formed aryl Grignard reagent XA is mixed with imide IX employing a molar ratio of imide IX to aryl Grignard reagent XA of within the range of from about 1:3 to about 1:1.1, preferably from about 1:1.4 to about 1:2.

To achieve desired optical purity in the final aldehyde III, it is preferred that the Grignard reaction be carried out employing ethylmagnesium chloride in a molar ratio to imide IX of within the range of from about 0.9:1 to about 1.2:1, preferably from about 1.0:1 to about 1.1:1. The ethyl-magnesium chloride will be employed in solution, preferably in THF, at a concentration of within the range of from about 1.0M to about 2.5M, preferably from about 1.5M to about 2.0M. The reaction of X with imide IX will be carried out at a temperature within the range of from about −78° C. to about 40° C., preferably from about −40° to about 20° C.

The ratio of desired to undesired diastereomers obtained using the above conditions will range from about 90:10 to >99:1.

Ethylmagnesium bromide may be employed in place of ethylmagnesium chloride with a resulting decrease in ratio of desired to undesired diastereomers for imides IX where R$_9$=OH.

Where the addition reaction of imide IX having R$_9$=OH to form intermediate XI is carried out employing the metallated aryl compound X where the metal is Li, imide IX is first treated with the alkyl lithium compound R$^a$Li employing a molar ratio of R$^a$Li:IX of within the range of from about 0.9:1 to about 1.2:1. The imide IX is then treated with the Li aryl compound XB employing a molar ratio of XB:IX of within the range of from about 1:1 to about 1:3.

The above reactions are carried out at a temperature within the range of from about −78° C. to about 40° C.

The alcohol XI resulting from the addition reaction, such as the Grignard reaction is then reduced employing a molar ratio of reducing agent:XI of within the range of from about 0.5:1 to about 3:1, preferably from about 0.8:1 to about 2:1.

The resulting amide XII is made to undergo lactonization employing a molar ratio of toluene:XII of within the range of from about 20:1 to about 10:1, preferably from about 16:1 to about 12:1. The toluene-XII mixture is heated to a temperature of within the range of form about 60° to about 120° C., preferably from about 110° to about 115° C. to form lactone XIIA. Lactone XIIA is treated with base:alcohol in a molar ratio of within the range of from about 0.1:1 to about 1.0:1, preferably from about 0.2:1 to about 0.4:1. The mixture is extracted with ethyl acetate and the aqueous layer is acidified with strong acid to achieve a pH of within the range of from about 1 to about 2.

The ethyl acetate wash may be treated with an acid such as oxalic acid and used to recrystallize starting material VII such as (S)-phenylglycinol.$(CO_2H)_2$.

The starting amine compounds VII wherein $R^9$ is other than OH are known in the art or may be prepared by conventional procedures.

Where in the starting amine compound VII, $R^9$ is OH, such compound may be prepared by reduction of an amino acid of the structure

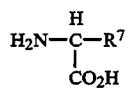

employing a mixture of sodium borohydride and sulfuric acid, or preferably $NaBH_4$ and $BF_3$ etherate ($BF_3$—$O(C_2H_5)_2$), in the presence of an inert organic solvent, such as THF or dimethoxyethane at a temperature of within the range of from about 60° to about 100° C.

The imide IX may also be prepared as shown in Reaction Schemes 6A, 6B and 6C.

In Reaction Scheme 6A, imide IX is prepared starting with maleic anhydride which is reacted with furan, under an inert atmosphere such as argon, employing a molar ratio of furan:maleic anhydride of within the range of from about 4:1 to about 20:1, preferably from about 5:1 to about 7:1, to form anhydride VIIa.

Anhydride VIIa is mixed with inert organic solvent such as n-butyl acetate, t-butyl acetate or xylene, under an inert atmosphere such as argon, and the resulting mixture is chilled and then reacted with a mixture of amine base such as triethylamine, diisopropylethylamine, or tributylamine, and amine VII, which includes at least one chiral center (which is attached directly to the nitrogen of the amine), employing a molar ratio of anhydride VIIa:amine VII of within the range of from about 0.9:1 to about 1:1, preferably about 1:1, to form amine XX (as a mixture of diastereomers). Amine XX is then reduced by reaction with hydrogen in the presence of a catalyst such as Pd-C, $Pd$-$BaSO_4$ or Pt-C to form amine XXII. The reaction mixture is filtered to remove catalyst and heated at a temperature within the range of from about 150° to about 170° C., preferably from about 155° to about 160° C., to remove amine base and water to form imide IX.

In a preferred embodiment, in amine VII, $R^7$ is phenyl, and $R^8$ and $R^9$ are each hydrogen.

In Reaction Scheme 6B, imide IX is prepared by a Dieis-Alder reaction of maleimide XXIII (which includes at least one chiral center) with furan employing a molar ratio of furan:XXIII of within the range of from about 2.5:1 to about 10:1, preferably from about 3:1 to about 4:1, in the presence of a Lewis acid, such as $AlCl_3$, $AlBr_3$, $FeBr_3$, $TiCl_4$, or $SnCl_4$, and inert organic solvent such as methylene chloride, dichloroethane or toluene, under an inert atmosphere such as argon, to form the exo adduct XXV. Exo adduct XXV is reduced by reaction with hydrogen in the presence of a catalyst such as Pd/C, $Pd$-$BaSO_4$, or Pt-C, in the presence of inert organic solvent, such as ethyl acetate, toluene or tetrahydrofuran, to form imide IX.

As shown in Reaction Scheme 6B, endo compound XXVA is formed together with exo compound XXV. During the reaction endo compound XXVA undergoes a selective retro Dieis-Alder reaction to form starting materials furan and imide XXIII which are further recycled to produce the thermodynamic exo product XXV.

The maleimide XXIII is prepared by reaction of maleic anhydride and amine VII (which includes at least one chiral center directly attached to the nitrogen of the amine) in the presence of an amine base such as triethyl amine or diisopropylethyl amine, acetic anhydride or other cyclizing agent such as propionic anhydride, and an inert organic solvent such as THF, ethylene glycol, dimethyl ether or toluene, at a temperature of within the range of from about 70° to about 120° C., preferably from about 80° to about 90° C., employing a molar ratio of maleic anhydride:amine VII of within the range of from about 0.9:1 to about 1.1:1, preferably about 1:1.

Maleimide XXIII may also be prepared from acid VIIB

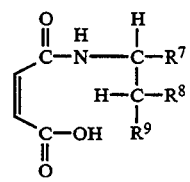

by treating VIIB with an amine base such as diisopropylamine, triethylamine or tributylamine in the presence of a silylating agent such as hexamethyldisilazane (HMDS), chlorotrimethylsilane (TMSCl), bissilylacetamide (BSA) or bissilylurea (BSU) and acetonitrile, n-butyl acetate or toluene, to form maleimide XXIII.

In carrying out the above reactions to form maleimide XXIII, the amine base will be employed in a molar ratio to VIIB of within the range of from about 1.2:1 to about 1.1:1, preferably about 1:1, while the silylating agent will be employed in a molar ratio to VIIB of within the range of from about 2:1 to about 1:1. These reactions are carried out at a temperature within the range of from about 60° to about 110° C.

The acid VIIB is prepared by reacting amine VII with maleic anhydride

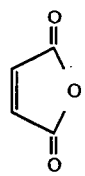

in the presence of acetonitrile, tetrahydrofuran (THF) or ethylacetate employing a molar ratio of maleic anhydride to VII of within the range of from about 0.9:1 to about 1.05:1, preferably about 1:1.

In Reaction Scheme 6C, imide XXXI is prepared in the latter part of Scheme 6C as follows: compound XXIX is reacted with hydrogen in the presence of a transition metal catalyst such as Pd/C, $Pd$-$BaSO_4$ or Pt-C, to form XXX, followed by deacetylation with alkali metal carbonate, such as $K_2CO_3$, $Li_2CO_3$ or $Na_2CO_3$, preferably $K_2CO_3$, to form XXXI.

Imide XXXI may then be employed to prepare compounds of formulae IA, IB and IC following Reaction Schemes 3, 1 and 4.

The compound XXIX is prepared as shown in the early part of Reaction Scheme 6C, wherein amine alcohol VIIA (which includes at least one chiral center and R[7] is preferably phenyl) is reacted with a silylating agent (employing a molar ratio of silylating agent:VIIA of within the range of from about 2.5:1 to about 5:1) such as bistrimethylsilyl urea (BSU), TMSCl/Et₃N, HMDS or bissilylacetamide (BSA), preferably BSU and an inert organic solvent such as tetrahydrofuran, glyme, EtOAc, CH₃CN or toluene, at a temperature within the range of from about 50° to about 70° C. The maleic anhydride (employing a molar ratio of anhydride:VIIA of within the range of from about 0.75:1 to about 3:1) is added and the mixture is heated to a temperature of within the range of from about 50° to about 70° C., to form silylated compound XXVII. XXVII is cyclized by treating with water and a catalyst for desilylation, such as n-tetrabutyl ammonium fluoride (TBAF), potassium fluoride or cesium fluoride, in the presence of a cyclizing agent such as acetic anhydride or propionic anhydride, and an amine base such as triethylamine, diisopropylethylamine or tributylamine, to form compound XXVIII. Compound XXVIII is reacted with furan (employing a molar ratio of furan:XXVIII of within the range of from about 30:1 to about 15:1) in the presence of inert organic solvent such as dichloromethane, dichloroethane or toluene to form predominantly the exo compound XXIX and endo compound XXIXA in minor amount. As shown, endo compound XXIXA in the presence of Lewis acid, such as any of the Lewis acids described above in Reaction Scheme 6B, forms exo compound XXIX.

The desilylating agent, such as TBAF, will be employed in a molar ratio to silylated compound XXVII of within the range of from about 0.05:1 to about 0.3:1, preferably from about 0.1:1 to about 0.2:1, while the cyclizing agent, such as the acid anhydride will be employed in a molar ratio to silylated compound XXVII of within the range of from about 5:1 to about 20:1, preferably from about 7:1 to about 10:1, and the base will be employed in a molar ratio to silylated compound XXVII of within the range of from about 5:1 to about 15:1, preferably from about 7:1 to about 10:1.

In a preferred embodiment in amine VIIA, R[7] is phenyl, and R[8] is hydrogen.

Alternatively, compound XXVIII may be prepared by treating amine alcohol VIIA with maleic anhydride (employing a molar ratio of alcohol:VIIA of within the range of from about 1.2:1 to about 1.1:1) in the presence of an inert organic solvent such as THF, toluene, monoglyme or ethylacetate, under an inert atmosphere such as argon at a temperature within the range of from about 20° to about 50° C., to form amide acid VIIC.

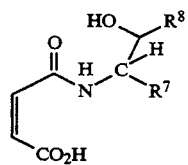

VIIC

The amide acid VIIC is cyclized by treatment with a cyclizing agent such as acetic anhydride or propionic anhydride (employing a molar ratio of anhydride:VIIC of within the range of from about 7:1 to about 5:1) and amine base such as triethylamine or diisopropylethylamine, in the presence of an inert organic solvent such as THF, toluene, monoglyme or ethylacetate, at a temperature within the range of from about 70° to about 110° C., to form compound XXVIII.

The halide compound

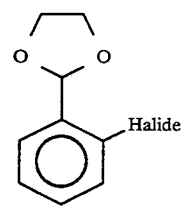

(for example, 2-(2-bromophenyl)-1,3-dioxolane) employed to prepare Grignard reagent XA used in Scheme 3 is prepared by reaction of the aldehyde

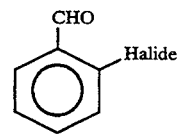

with ethylene glycol and p-toluenesulfonic acid in the presence of an aromatic solvent such as toluene, benzene or xylene, under an inert atmosphere such as nitrogen, at a temperature within the range of from about 80° to about 150° C., preferably at reflux.

In carrying out the preparation of the thromboxane receptor antagonist products IB and IC, as shown in Scheme 4, amide XIII is employed in a molar ratio to acid IIA of within the range of from about 1.5:1 to about 1:1, preferably from about 1.1:1 to about 1:1, to form amide XIV. Amide XIV is mesylated employing a molar ratio of methanesulfonyl chloride:XIV of within the range of from about 2:1 to about 1:1, preferably from about 1.3:1 to about 1:1 and a temperature within the range of from about −20° to about 60° C., preferably from about 0° to about 25° C.

The resulting mesylate XV is cyclized employing a molar ratio of triethylamine or other organic base:XV of within the range of from about 4:1 to about 2:1, preferably from about 3.5:1 to about 2.5:1, to form oxazoline XVI. Other organic bases which may be employed include diisopropylethylamine, pyridine or 2,6-lutidine.

The cupric bromide oxidation of oxazoline XVI is carried out at a temperature of within the range of from about 20° C. to about 70° C., employing a molar ratio of cupric bromide to oxazoline XVI of within the range of from about 2:1 to about 6:1 and a molar ratio of cupric bromide to DBU of within the range of from about 1:1 to about 1:3 in an inert solvent, preferably methylene chloride or acetonitrile. The oxidation is preferably carried out in the presence of a base such as hexamethylenetetramine which is disclosed in U.S. Pat. No. 5,281,716, which is incorporated herein by reference.

The so-formed oxazole ester IA may then be hydrolyzed employing conventional techniques such as treatment with an aqueous solution of an alkali metal base and then aqueous acid to form the corresponding acid IB which may be treated with sodium methoxide, sodium 2-ethylhexanoate or sodium ethoxide to form salt IC in the presence of acetone/methanol.

The term "lower alkyl" or "alkyl" as employed herein includes both straight and branched chain radicals of up to 18 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1, 2 or 3 substituents such as halo, alkenyl, alkynyl, aryl, alkyl-aryl, haloaryl, cycloalkyl, or alkylcycloalkyl.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with substituents such as halogen, lower alkyl, and/or alkoxy groups.

The term "aryl" or "Ar" as employed herein refers to monocyclic or bicyclic aromatic groups containing from 6 to 10 carbons in the ring portion, such as phenyl or naphthyl. Aryl (or Ar), phenyl or naphthyl may include substituted aryl, substituted phenyl or substituted naphthyl, which may include 1 or 2 substituents on either the phenyl or naphthyl such as lower alkyl,trifluoromethyl, halogen (Cl, Br, I or F), alkylsulfonyl, and/or arylsulfonyl.

The term "aralkyl", "aryl-alkyl" or "aryl-lower alkyl" as used herein refers to lower alkyl groups as discussed above having an aryl substituent, such as benzyl.

The term "lower alkoxy", "alkoxy" or "aralkoxy" includes any of the above lower alkyl, alkyl or aralkyl groups linked to an oxygen atom.

The term "halogen" or "halo" as used herein refers to Cl, Br, F or I, with Cl preferred.

The final compounds IB and IC prepared by the method of this invention are thromboxane receptor antagonists and as such are useful as inhibitors of thromboxane receptor mediated actions. The term "thromboxane receptor antagonist" includes compounds which are so-called thromboxane $A^2$ receptor antagonists, thromboxane $A^2$ antagonists, thromboxane $A^2$/-prostaglandin endoperoxide antagonists, TP-receptor antagonists, or thromboxane antagonists.

The compounds prepared by the method of the invention are also thromboxane synthetase inhibitors and thus are useful as inhibitors of thromboxane production.

Examples of various utilities of the compounds prepared by the method of the invention are set out in U.S. Pat. No. 5,100,889.

The following Examples represent preferred embodiments of the present invention. Unless otherwise indicated, all temperatures are expressed in degrees Centigrade.

Example 1

[2S- (2α, 3α, 4β, 7β, 7aα)]-2-(Octahydro-3-oxo-4,7-epoxy-isobenzofuran-1-yl)benzaldehyde A. (S)-β-Aminobenzeneethanol A one-liter three-necked flask equipped with a mechanical stirrer, reflux condenser and an addition funnel was charged with sodium borohydride (18.7 g, 0.495 mole), (S)-(+)-2-phenylglycine (Aldrich) (30 g, 0.198 mole) and THF (200 mL). The slurry was stirred vigorously at room temperature under argon. The addition funnel was charged with boron trifluoride etherate (54 mL, 0.439 mole), which was then added dropwise to the slurry over 35 minutes. The reaction began to reflux during the addition with no external heating. After the addition was complete, the reaction was heated to reflux for 20 hours.

The reaction was cooled to room temperature. Methanol (60 mL) was added dropwise through the dropping funnel over 45 minutes. The reaction bubbled vigorously and began to reflux with no external heating. Sodium hydroxide (5N, 200 mL) was added. At this point the slurry dissolved to give a cloudy white solution. The reflux condenser was replaced with a distillation head and the solvents which boiled at less than 100° C. were removed by distillation (~260 mL) and discarded. The distillation head was replaced with a reflux condenser and the reaction was heated to reflux for three hours, then allowed to cool to room temperature.

The mixture was extracted with ethyl acetate (1×150 mL, then 2×100 mL). The combined organic layers were washed with aqueous saturated NaCl (1×100 mL), dried over magnesium sulfate, filtered and concentrated on a rotary evaporator (bath temp. 30° C. and vacuum of ~5 mm. Hg) to provide 26.8 g (99%) of crude title compound as an off white solid.

The above crude title compound was dissolved in boiling ethyl acetate (150 mL). Hexane (150 mL) was added with heating and stirring. The solution was allowed to cool with stirring. After 18 hours at room temperature, the crystals were filtered, washed with 1:1 ethyl acetate:hexane (3×30 mL), hexane (3×30 mL) and dried to provide 14.6 g (54%) of title compound as a white solid, mp 75°–77° C. A second crop (7.79 g, 29%) and a third crop (1.34 g, 5%) provided additional title compound. The total yield of title compound was 23.7 g (88%).

B. [2(S),3aα,4β, 7aβ,7aα]-Hexahydro-2-(2-hydroxy-1-phenylethyl)-4,7-epoxy-2H-isoindole-1,3-dione Into a 2.0 L 3-necked flask was charged (3aα,4β,7β,-7aα)-hexahydro-4,7-epoxyisobenzofuran-1,3-dione (Lancaster) (34.1 g, 0.203 mol), Part A (S)-β-aminobenzeneethanol (27.8 g, 0.203 mol) and oxalic acid (18.3 g, 0.203 mol). The above mixture was suspended in THF (500 ml). To the above suspension was added triethylamine (Et₃N) (56 ml) and the resulting mixture was heated to reflux for 8.0 h. The reaction mixture was cooled to room temperature and poured into sat. NaHCO₃ (300 ml). The resulting mixture was extracted with ethyl acetate (2×300 ml). The organic extracts were combined, dried over MgSO₄ and concentrated in vacuo on the rotovap at a bath temp. of 35° C. under ~1.5 mm Hg. The residue was dissolved in ethyl acetate (100 ml) at 60 ° C. and hexanes (50 ml) were added. The resulting solution was allowed to cool to room temperature and put into a cold room for 14 h. The white solid was filtered using a medium porosity fritted glass filter and dried in a vacuum oven (~80mm Hg) for 24 h to give title compound (48.7 g, 84%).

C. 2-(2-Bromophenyl)-1,3-dioxolane

A 12 L 3-necked flask fitted with an overhead stirrer was charged with 2-bromobenzaldehyde (800 g, 4.324 moles), ethylene glycol (402.6 g, 6.485 moles), p-toluenesulfonic acid. H₂O (3.95 g, 0.021 moles) and toluene (3.785 kg, 41.074 moles).

One side of the flask was stoppered (glass) and a Dean-Stark separator/condenser/N₂ port was attached to the other side.

The heterogeneous yellow reaction mixture was stirred under a nitrogen atmosphere and heated to reflux for about 45 minutes.

Water was collected via the Dean-Stark separator and the residue was cooled to room temperature and washed with 1.2 L of saturated aqueous NaHCO₃ followed by 1.2 L of saturated aqueous NaCl.

The combined organic layers were dried over anhydrous MgSO4, filtered, concentrated on a rotary evaporator and dried under high vacuum to provide title compound in the form of an oil. The so-formed oil was vacuum distilled to provide 52 g and 876.2 g of title compound (88.9% yield).

D.

[2S-(2α,3aα,4β,7β,7aα)]-2-(Octahydro-3-oxo-4,7-epoxyisobenzofuran-1-yl)benzaldehyde Into an oven-dried, argon purged 500 ml flask, Part C 2-(2-bromophenyl)-1,3-dioxolane (71.5 g, 0.313 mol) was dissolved in THF (240 ml). Magnesium turnings (11.4 g, 0.467 mol) were charged into a separate oven-dried, argon-purged 500 ml 3-necked flask equipped with a condenser. To this flask was added a portion (10.0 ml) of the above solution at room temperature. The reaction initiated by itself after stirring for 5 min. The rest of the solution was added into the flask at such a rate to maintain a gentle reflux. After all of the solution had been added, the reaction mixture was stirred for an additional 2.0 h at room temperature to give the aryl Grignard reagent bromo[2-(1,3-dioxolan-2-yl)phenyl]magnesium.

The Part B imide (50.0 g, which included 2 g from a previous batch, 0.174 mol) was added to an oven-dried, argon purged 3.0 L 3-necked flask equipped with an addition funnel, dissolved in THF (790 ml), and cooled to −15° C. in an ice-methanol bath. To this solution was added C2H5MgCl (87.0 ml of a 2.0M solution in THF) dropwise over a period of 0.5 hour via the addition funnel. After the addition was complete, the reaction was stirred for 0.5 hour at −15° C. The ice-methanol bath was removed and replaced with an ice-water bath. The reaction mixture was stirred for an additional 0.5 hour at 0° C. To this mixture was added dropwise over a period of 1.0 hour the above aryl Grignard solution (280 ml of a 1.12M solution in THF, 0.313 mol). After the addition was complete, the reaction was stirred at 0° C. for 3.0 h. The ice-water bath was removed and the reaction was stirred for an additional 4.5 h. The reaction mixture was cooled to 0° C. with an ice-water bath and quenched by adding ethanol (1.0 L).

To the resulting mixture was added solid NaBH4 (15.0 g, 0.397 mol) in 6 equal portions over 0.5 hour. The ice-water bath was allowed to melt and the reaction mixture was allowed to warm to room temperature and stirred for 14 h. The reaction mixture was poured into 10% Na2CO3 (1.5 L) and the mixture was extracted with ethyl acetate (3×1.5 L). The organic extracts were combined, washed with brine (1.5 L), dried over MgSO4, filtered and concentrated in vacuo on the rotary evaporator as described above to obtain the crude [1R-[1α,2α(S*),3aα,4α]-3-[[2-(1,3-dioxolan-2-yl)phenyl]hydroxymethyl]-N-(2-hydroxy-1-phenylethyl)-7-oxabicyclo[2.2.1]heptane-2-carboxamide (104.0 g, 110%) which was used in the next step without any additional purification.

The above crude alcohol (104.0 g) was dissolved in toluene (250 ml) and heated to reflux for 3.0 h. The resulting solution was cooled to room temperature and then 1N NaOH (750 ml) and ethanol (150 ml) were added. The mixture was vigorously stirred for 4.0 h at room temperature and then was extracted with ethyl acetate (750 ml). The aqueous layer was mixed with THF (125 ml). To this mixture was added 10% HCl (350 ml) at room temperature. The resulting mixture was then stirred at room temperature for 14 h during which time a white precipitate formed. The reaction was cooled to 0° C. for 1.0 hour. The white precipitate was filtered off using a medium porosity fritted glass filter and washed with water (100 ml). The solid was dried under high vacuum to give the title compound as a white solid (32.0 g, 71%) with 99.9% ee as determined by chiral HPLC.

Example 2

Alternative Preparation of [2S-(2α,3aα,4β,7β,7aα)]-2-(Octahydro-3-oxo-4,7-epoxyisobenzofuran-1-yl)benzaldehyde

A.

[2(S),3aα,4β,7β,7aα]-Hexahydro-2-[1-(hydroxymethyl)-2-methylpropyl]-4,7-epoxy-2H-isoindole-1,3-dione A 3 L 3-necked Morton flask, fitted with a condenser and a mechanical stirrer, was purged with a steady stream of argon for 1 hour. The flask was then charged with S-(+)-2-amino-3-methyl-1-butanol (50.0 g, 485 mmole) and THF (1000 mL). The resulting mixture was stirred for 5 minutes until a homogeneous solution was obtained. Oxalic acid (43.1 g, 479 mmole) was added in one portion. Within 5 minutes a thick, white precipitate formed. An additional portion of THF (500 mL) was added to the flask. (3aα,4β,7β,7aα)-Hexahydro-4,7-epoxyisobenzofuran-1,3-dione (anhydride) (77.0 g, 458 mmole) was added in one portion, followed by triethylamine (129 mL, 926 mmole). The mixture was heated to reflux for 18 hours, then allowed to cool to room temperature. The resulting slurry was filtered, and the filtrate concentrated on a rotary evaporator to a volume of ~1L. The solution was poured into saturated aqueous NaHCO3 (1L) and extracted with CH2Cl2 (1×1000 mL, then 2×500 mL). The combined organic layers were dried over anhydrous MgSO4, filtered, concentrated on a rotary evaporator, and dried under high vacuum to provide 94.8 g of crude title imide.

The above crude imide (94.8 g) was dissolved in hot ethyl acetate (250 mL) and diluted with hexane (570 mL) at reflux. The mixture was allowed to cool to room temperature. The resulting crystals were collected by suction filtration, washed with 2.4:1 hexane/ethyl acetate (2×100 mL) and hexane (2×100 mL). The material was transferred to a vacuum oven and dried for 2 days under house vacuum (~80 mm Hg) at ambient temperature to provide 78.6 g (68%) of title imide. The mother liquor was concentrated on a rotary evaporator. A second crop of 9.7 g (8%) was obtained from ethyl acetate (40 mL) and hexane (120 mL). The total yield of title alcohol was 88.3 g (76%).

B.

[2S-(2α,3aα,4β,7β,7aα)]-2-(Octahydro-3-oxo-4,7-epoxyisobenzofuran-1-yl)benzaldehyde In a flame-dried, argon purged 250 mL 3-necked flask, fitted with a condenser and a dropping funnel, was placed magnesium shot (2.25 g, 92.6 mmole) and freshly distilled THF (80 mL). The THF suspension was heated to reflux and a small crystal of iodine was added to the flask. 2-(2-Bromophenyl)-1,3-dioxolane (18.45 g, 80.5 mmole) was added at such a rate as to maintain vigorous refluxing. Once the addition was complete (~20 minutes), reflux was maintained with the aid of a heating mantle for an additional 25 minutes.

The mixture was then allowed to cool to room temperature.

In a flame dried 500 mL flask was added Part A compound (10.00 g, 40.3 mmole) and THF (60 mL). The mixture was cooled in a −20° C. bath and ethylmagnesium chloride (21.2 mL of a 1.90M solution in THF, 40.3 mmol) was added dropwise to the solution at such a rate so that the internal temperature did not exceed −10° C. The mixture was then immediately cooled in a −78° C. bath and the Grignard solution of 2-(2-bromophenyl)-1,3-dioxolane (62.7 mL) was added via syringe at such a rate that the internal temperature did not exceed −65° C. The dry ice was removed from the −78° C. bath and the mixture was allowed to slowly warm to room temperature with stirring over 5 hours. After stirring at room temperature for 15 minutes, TLC indicated that no starting material remained; a new material predominated. The mixture was quenched with absolute ethanol (145 mL) and sodium borohydride (3.05 g, 80.5 mmole) was added in one portion. The mixture was stirred at room temperature for 1 hour. TLC indicated the reduction to be complete. The mixture was carefully poured into aqueous saturated $Na_2CO_3$ (500 mL) and extracted with $CH_2Cl_2$ (2×500 mL). The combined organic layers were dried over $MgSO_4$, filtered, concentrated on a rotary evaporator, and dried under high vacuum at room temperature to provide 18.1 g ( 112% ) of crude [1R-[1α,2α(S*),3aα,4α]-3-[[2-(1,3-dioxolan-2-yl) phenyl]hydroxymethyl]-N-[1-(hydroxymethyl)-2-methylpropyl]-7-oxabicyclo[2.2.1]heptane-2-carboxamide which was used in the next step without any additional purification.

The above crude alcohol (18.1 g) was dissolved in toluene (80 mL) and heated to reflux for 1.5 hours. TLC indicated the formation of a new material. The mixture was cooled to room temperature with an ice-bath and diluted with ethanol (20 mL) and 1.0M NaOH (80 mL). The mixture was stirred at room temperature for 4.5 hours. The layers were separated and the aqueous layer was washed with $CH_2Cl_2$ (2×100 mL). The aqueous layer was diluted with isopropyl alcohol (20 mL) and then adjusted to pH 1.05 with 1.0M HCl (120 mL). The mixture was stirred at room temperature for 18 hours, then diluted with THF (180 mL, added in 60 mL increments over 7 hours) until the mixture was homogeneous. The solution was stirred at room temperature overnight, and concentrated on a rotary evaporator to remove volatile organics (160 mL). A white solid formed during concentration. The material was filtered and washed with water (3×100 mL). The cake was dried in vacuo to provide 6.9 g (66.7% yield) of the title aidehyde. Chiral HPLC analysis revealed the material to be a 96:4 mixture of enantiomers.

Example 3

[1S-(1α,2α,3α,4α)]-2-[[2-(3-Methoxy-3-oxopropyl)-phenyl]methyl]-7-oxabicyclo[2.2.1]heptane-3-carboxylic acid (via Scheme 1)

A.
[1S-[1α(E),3aα,4β,7β,7aβ]]-3-[2-(Octahydro-3-oxo-4,7-epoxyisobenzofuran-1-yl)phenyl]-2-propenoic acid, methyl ester In a 250 mL flask was placed Example 1 aldehyde (obtained from two different batches) (9.44 g, 36.54 mmole), lithium chloride (1.7 g, 40.19 mmole) and acetonitrile (145 mL). The solution was stirred magnetically under an argon atmosphere. Trimethylphosphonoacetate (7.32 g, 40.19 mmole) was added via syringe followed by 1,8-diazabicyclo-[5.4.0]undec-7-ene (DBU) (6.01 mL, 40.19 mmole). The solution became cloudy and the temperature of the reaction rose to 42° C. After 75 minutes, TLC indicated the reaction to be complete. The mixture was poured into aqueous saturated sodium bicarbonate (500 mL) and extracted with methylene chloride (2×500 mL). The combined organic layers were dried over anhydrous magnesium sulfate, filtered, concentrated on a rotary evaporator (bath temp. 35° C., ~80 mm Hg) and dried under high vacuum (~0.5 mm Hg) at room temperature to provide 11.36 g (98.9% yield) of the crude title compound as a yellow, crystalline solid.

B. [1S-(1,60,2α,3α,4α)]-2-[[2-(3-Methoxy-3-oxopropyl)phenyl]methyl]-7-oxabicyclo[2.2.1]-heptane-3-carboxylic acid The Part A crude vinyl ester (11.36 g) was placed in a 250 mL flask and dissolved in THF (35 mL) and methanol (70 mL). To the magnetically stirred solution was added Pearlman's catalyst (Aldrich) $(Pd(OH)_2/C)$ (1.14 g). The flask was evacuated, then connected to a balloon filled with hydrogen. The reaction mixture was stirred at room temperature for 2 hours, and then a second portion of Pearlman's catalyst (1.14 g) was added. The flask was re-evacuated and reconnected to the balloon filled with hydrogen. The mixture was stirred at room temperature for an additional 2 hours. TLC indicated complete conversion to the title compound. The balloon was removed and Celite (2.0 g) was added to the mixture and stirred for 10 minutes. The mixture was filtered through a pad of Celite (45×25 mm). The pad was washed with methanol (50 mL). The filtrate was concentrated on a rotary evaporator as described above to provide a yellow oil. The oil was dissolved in methylene chloride (100 mL) and dried over anhydrous magnesium sulfate. The solution was filtered, concentrated on a rotary evaporator as described above, and dried under high vacuum (~0.5 mm Hg) to provide 11.81 g (101.6% yield) of the crude title compound.

The above crude title compound (11.81 g) was dissolved in hot ethyl acetate (23 mL) and diluted with hot heptane (46 mL). The mixture was allowed to cool while being stirred magnetically. The mixture was seeded at a temperature of 58° C. with crystals of the title compound. Upon cooling to room temperature, a significant quantity of the title compound had crystallized from the solution. An additional portion of heptane (65 mL) was added and the mixture was stirred for 5 minutes. The mixture was allowed to stand at room temperature overnight. The resulting solid was collected by suction filtration, washed with heptane (50 mL), then dried under high vacuum at room temperature to provide 7.32 g (62.9% yield) of the title compound containing small traces of yellow material.

The solid and the mother liquor were recombined and dissolved in ethyl acetate (120 mL) and treated with Darco KB activated carbon (1.2 g). The mixture was heated to reflux for 2 minutes, then allowed to cool to room temperature. Celite (2.4 g) was added, and the mixture was stirred for 10 minutes, then filtered through a pad of Celite (45×25 mm). The pad was washed with ethyl acetate (50 mL). The filtrates were concentrated on a rotary evaporator as described above to provide a pale yellow oil. The oil was dissolved in ethyl acetate (23 mL), heated to reflux and diluted with heptane (46 mL). The mixture was then allowed to cool to room temperature with stirring. The mixture was seeded with crystals of the title compound. After stirring at room temperature for ~15 minutes, additional heptane (65 mL) was added. The flask was placed in a cold room (~4° C.) overnight. The resulting crystals were collected by suction filtration, washed with heptane (50 mL) and dried under high vacuum (~0.5 mm Hg) at room temperature to provide 9.97 g (85.7% yield) of the title compound.

Example 4

[1S-(1α,2α,3α,4α)]-2-[[-(3-Methoxy-3-oxopropyl)-phenyl]methyl]-7-oxabicyclo[2.2.1]heptane-3-carboxylic acid (via Scheme 2)

A. [1S-[1α(E),3aα,4β,7β,7aα]]-3-[2-(Octahydro-3-oxo-4,7-epoxyisobenzofuran-1-yl)phenyl]-2-propenoic acid A dry, argon purged 250 mL one-necked flask was charged with Example 1 aldehyde (10 g, 38.8 mmole), malonic acid (18.1 g, 174 mmole) and pyridine (20 mL). The flask was equipped with a reflux condenser and the mixture was heated at 85° C. in an oil bath. The solids dissolved after heating for ten minutes. Piperidine (0.380 mL) was added. The reaction was stirred at 85° C. for 18 hours and cooled to room temperature. 10% HCl (200 mL) was added over 15 minutes. The solution became thick with the formation of a precipitate. The slurry was stirred at room temperature for three hours. The solid was collected in a medium scintered glass funnel and washed with water (3×30 mL). A clean 500 mL receiving flask was attached to the funnel. Acetone (~240 mL) was added to dissolve the solid and was then pulled through the funnel. The filtrate was concentrated on a rotary evaporator to provide 10.8 g (93%) of the crude title acid as a white solid which was used in the next step without any additional purification.

B. [1S-[1α(E),3aα,4β,7β,7aα]]-3-[2-(Octahydro-3-oxo-4,7-epoxyisobenzofuran-1-yl)phenyl]-2-propenoic acid, methyl ester The above crude Part A acid (10.7 g, 35.7 mmole) was mixed with methanol/sulfuric acid (80:1) (360 mL) at room temperature under argon in a 500 mL 2-necked flask equipped with a reflux condenser. The mixture was heated to 50° C. in an oil bath. As it warmed, the solids dissolved. After six hours, the solution was cooled to room temperature and concentrated on a rotary evaporator to a slurry (~50 mL). The slurry was diluted with ethyl acetate (100 mL). The solution was washed with aqueous saturated sodium bicarbonate (3×25 mL) and aqueous saturated NaCl (1×25 mL). The organic layer was dried over magnesium sulfate, filtered and concentrated on a rotary evaporator to provide 10.6 g (95%) of the crude title ester as an off-white, hard solid which was used in the next step without any additional purification.

C. [1S-(1,60 2α,3α,4α)]-2-[[2-(3-Methoxy-3-oxopropyl)phenyl]methyl]-7-oxabicyclo[2.2.1]heptane-3-carboxylic acid The above crude Part B ester (10.3 g, 32.8 mmole) was dissolved in a solution of THF (40 mL) and methanol (80 mL) in a 250 mL one-necked flask equipped with a three-way valve. The valve was connected to a balloon of hydrogen and the house vacuum. The flask was evacuated and filled with hydrogen three times by turning the valve. Pearlman's catalyst (1.03 g, 10% by weight) was added. The flask was again evacuated and filled with hydrogen three times. The reaction was stirred at room temperature for two hours.

Celite (15 g) was added to the flask and stirred for 10 minutes. The mixture was filtered through a pad of Celite and concentrated on a rotary evaporator. The residue had a grey color. It was dissolved in methylene chloride (50 mL), dried over magnesium sulfate and filtered through another pad of Celite. The filtrate was concentrated on a rotary evaporator. The product was again dissolved in methylene chloride (25 mL) and filtered through a thick pad of Celite to provide a clear, yellow solution. The solvent was removed on a rotary evaporator to provide 10.4 g (99%) of the crude title acid as a mixture of a white solid, a colorless oil and a dark yellow oil.

The crude product was dissolved in boiling ethyl acetate (25 mL). While boiling, heptane (50 mL) was added slowly to maintain reflux. The clear, pale yellow solution was then allowed to cool to room temperature with stirring. The mixture was seeded with crystals of the title acid when it reached 50° C., and again when it reached 45° C. The mixture became cloudy and then thick with solids. After the mixture had reached room temperature (~28° C.), additional heptane (70 mL) was added. The flask was placed in a cold room (~4° C.) over the weekend. The resulting crystals were collected by suction filtration, washed with heptane (3×50 mL) and dried under house vacuum at room temperature for 24 hours to provide 9.22 g (88%) of the title acid as a fluffy white solid. The overall yield from Example 1 aldehyde was 77.8%.

Example 5

N-Pentyl-L-Serinamide

A. Carbobenzyloxy-L-serine

L-Serine (20.00 g, 190.3 mmol) was dissolved in water, and aqueous sodium hydroxide was added to adjust the pH of the solution to about 8.5 while maintaining the temperature at about 25° C. Benzyl chloroformate (36.0 g, 211.0 mmol) was added while the pH was maintained between 8.3 and 8.5 by the addition of aqueous sodium hydroxide and the temperature was maintained at about 30° C. The mixture was stirred for about 2 hours. The reaction mixture was extracted with methylene chloride. The phases were separated, and the pH of the aqueous phase was adjusted to about 7 with concentrated hydrochloric acid. The aqueous phase was heated to about 40° C. under low vacuum to remove any residual methylene chloride. Water was added and the aqueous solution was heated to about 60° C. The pH was adjusted to about 2 with concentrated hydrochloric acid while maintaining the temperature at about 60° C. The solution was cooled to about 50° C. while stirring and seed crystals were added. With stirring, cooling was continued to about 0° C. to complete the crystallization. The product was collected and the cake was washed with cold (about 5° C.) water. The product was dried under vacuum at about 40° C. to afford carbobenzyloxy-L-serine.

B. N-Pentyl-L-serinamide, oxalate (1:1) salt

Under an inert atmosphere, 1,8-diazabicyclo[5.4.0]undec-7-ene (5.10 g, 33.5 mmol) was added to a suspension of Part A carbobenzyloxy-L-serine (7.50 g, 31.4 mmol)

in ethanol. Ethyl acetate was added and the mixture was agitated (optionally, with heating up to about 50° C.) to obtain a clear solution. Pyridine (0.25 g, 3.2 mmol) was added and the mixture was cooled to about −30° C. Trimethylacetyl chloride (4.12 g, 34.2 mmol) was added and the mixture was maintained at about −30° C. With cooling, n-amylamine (3.00 g, 34.4 mmol) was added and the mixture was stirred at about −10° C. for about 2 hours. Cooling was discontinued and aqueous phosphoric acid was added. The mixture was warmed to about 10° C. and the phases were separated. The organic solution was washed sequentially with aqueous phosphoric acid, aqueous potassium carbonate, and brine. Throughout these extractions, the aqueous phase was back extracted with ethyl acetate. The combined organic solution was distilled under vacuum at about 25° C. while ethanol was added until all of the ethyl acetate was removed. Under an inert atmosphere, 10% palladium on carbon (50% water, 0.75 g) was added. The resulting mixture was purged with nitrogen and then stirred in the presence of hydrogen at about 25° C. for about 6 hours. The catalyst was removed by filtration, and the clear filtrate was partially concentrated under vacuum at about 30° C. The concentrated filtrate was added to a solution of oxalic acid dihydrate (4.35 g, 34.5 mmol) in ethanol and water and a thick precipitate was formed. The suspension was heated to reflux to obtain a clear solution. Water was added at the reflux temperature until a slight turbidity was observed. The mixture was cooled to about 0° C. and stirred until crystallization was complete (about 1 hour). The product was collected and the cake was washed with ethanol. The product was dried under vacuum at about 25° C. to afford the title compound.

Example 6

[1S-(1α,2α,3α,4α)]-2-[[3-[4-[(Pentylamino)carbonyl]-2-oxazolyl]-7-oxabicyclo[2.2.1]hept-2-yl]methyl]-benzenepropanoic acid, monosodium salt A.
[1S-[1α,2α,3α(R*),4α]]-2-[[3-[[[1-(Hydroxymethyl)-2-oxo-2-(pentylamino)ethyl]amino]carbonyl]-7-oxabicyclo[2.2.1]-hept-2-yl]methyl]benzenepropanoic acid, methyl ester Under an inert atmosphere, a catalytic amount of dimethylformamide (0.067 mL, 0.87 mmol) was added to a solution of Example 3 carboxylic acid (6.66 g, 20.9 mmol) in toluene and the resulting mixture was cooled to about 0° C. While maintaining the temperature below 0° C., oxalyl chloride (2.96 g, 23.3 mmol) was added and the mixture was stirred at about 5° C. for about 3 hours. The resulting acid chloride solution was partially concentrated under vacuum at about 40° C. and then used in the coupling reaction described below.

Meanwhile, Example 5 amide (6.17 g, 23.3 mmol) was added to a solution of sodium bicarbonate (9.63 g, 115 mmol) in water while the temperature was maintained at about 20° C. Methyl ethyl ketone was added and the biphasic mixture was cooled to about 0° C. While maintaining the temperature at about 0° C., the previously prepared acid chloride solution was added with stirring. The mixture was stirred at about 5° C. for about 20 hours and then heated to about 60° C. and the phases were allowed to separate. The organic phase was washed at about 50° C. sequentially with saturated sodium bicarbonate solution, aqueous phosphoric acid, and brine. The organic solution was partially concentrated under vacuum at about 40° C. to obtain a thick suspension. n-Heptane was added and the resulting mixture was cooled to about 20° C. with stirring. The product was collected and the cake was washed with n-heptane. The product was dried under vacuum at about 35° C. to afford the title ester.

B.
[1S-[1α,2α,3α(R*),4α]]-2-[[3-[4,5-Dihydro-4-[(Pentylamino)carbonyl]-2-oxazolyl]-7-oxabicyclo[2.2.1-]hept-2-yl]methyl]benzenepropanoic acid, methyl ester Under an inert atmosphere, Part A ester (7.00 g, 14.7 mmol) was dissolved in dry dimethylformamide. The moisture content of the resulting solution must be <0.1% w/w; if it was higher, the solution was first dried by vacuum distillation of a portion of the solvent and dry dimethylformamide was added to restore the original solution volume. Triethylamine (4.29 g, 42.4 mmol, plus approximately 1 mmol per mmol of water measured in the Part A ester solution) was added and the mixture was cooled to about 0° C. While maintaining the temperature below 5° C., methanesulfonyl chloride (2.02 g, 17.6 mmol, plus approximately 0.4 mmol per mmol of water measured in the Part A ester solution) was added. The reaction mixture was stirred at about 5° C. for about 5 hours. The mixture was warmed to about 25° C. and stirred for about 20 hours. Cold (about 5° C.) water was added while maintaining the pH at about 8.0 by the addition of aqueous phosphoric acid. The resulting suspension was stirred at about 10° C. for about 1 hour. The product was collected and the cake was washed with cold (about 5° C.) water. The product was dried under vacuum at about 25° C. to afford the title compound.

C. [1S-(1α,2α,3,4α)]-2-[[3-[4-[(Pentylamino) carbonyl]-2 -oxazolyl]-7-oxabicyclo [2.2.1]hept -2-yl]methyl]benzenepropanoic acid, methyl ester Under an inert atmosphere, hexamethylenetetramine (5.89 g, 42.0 mmol) was added to a mixture of copper (II) bromide (8.63 g, 38.6 mmol) and methylene chloride. A solution of 1,8-diazabicyclo[5.4.0]undec-7-ene (6.38 g, 41.9 mmol) in methylene chloride was added with slight cooling to maintain the temperature at about 30° C. A solution of Part B ester (4.50 g, 9.86 mmol) in methylene chloride was added, and the reaction mixture was stirred at about 30° C. for about 14 hours. The mixture was cooled to about 20° C. and filtered, and the cake was washed with methylene chloride. At this point, the filtrate may be combined with the filtrate from another run. The filtrate was concentrated under vacuum at about 30° C., and ethyl acetate, water and aqueous ammonia were added to the resulting residue. The phases were separated, and the organic phase was washed with a mixture of water and aqueous ammonia. The resulting aqueous solution was back extracted with ethyl acetate. The combined organic phase was washed sequentially with aqueous phosphoric acid and brine. Brine was added to the organic phase and the pH was adjusted to about 7 with saturated sodium bicarbonate. The organic solution was separated and partially concentrated under vacuum at about 40° C. Seed crystals of the title compound were added followed by n-heptane. The remaining ethyl acetate was replaced with n-heptane by a vacuum-distillation exchange procedure at a temperature of 40° C. or below. The product was collected and the cake was washed with n-heptane. The product was dried under vacuum at about 25° C. to afford the title compound.

D. [1S-(1α,2α,3α,4α)]-2-[[3-[4-[(Pentylamino)carbonyl]-2-oxazolyl]-7-oxabicyclo[2.2.1]hept-2-yl]methyl]benzenepropanoic acid, monosodium salt Under an inert atmosphere, 1N sodium hydroxide (3.6 mL, 3.6 mmol) was added to a cold 5 (about 5° C.) solution of Part C ester (0.600 g, 1.32 mmol) in tetrahydrofuran. The reaction mixture was stirred at about 25° C. for about 4 hours. The reaction mixture was partially concentrated under vacuum at about 35° C. The concentrated solution was diluted with water and then washed with diethyl ether. The phases were separated and the pH of the aqueous solution was adjusted to about 7 with concentrated hydrochloric acid. Methylene chloride was added and acidification was continued with stirring to a pH of about 2. The phases were separated and the aqueous layer was extracted with methylene chloride. The resulting combined organic extract was washed sequentially with water and brine. The organic solution was dried over anhydrous magnesium sulfate, filtered and concentrated under vacuum at about 25° C. to a solid. The resulting solid was dissolved in hot (about 90° C.) acetonitrile, and the solution was allowed to stand at room temperature without stirring for about 12 hours. The product was collected and the cake was washed with cold (about 5° C.) acetonitrile. The product was dried under vacuum at about 35° C. to afford the title compound.

Under an inert atmosphere, the title compound (461 g, 1.04 mol) was dissolved in acetone at about 50° C. The resulting solution was cooled to about 35° C. and a solution of 25% w/w sodium methoxide in methanol (0.264 mL, 1.15 mol) was added. The resultant slurry was allowed to cool to about 25° C. with stirring. The product was collected and the cake was washed with acetone. The product was dried under vacuum at about 35° C. to afford the title compound.

Example 7

[2S-(2α,3aα,4β,7β,7aα)]-2-(Octahydro-3-oxo-4,7-epoxy-isobenzofuran-1-yl) benzaldehyde A. [2(S),3α,4β,7β,7α]-Octahydro-2-(2-phenylethyl)-4,7-epoxy-1H-isoindole-1,3(2H)-dione An argon purged 500 mL one-necked flask was charged with (3aα,4β,7β,7aα)-hexahydro-4,7-epoxyisobenzofuran -1,3-dione (10.0 g, 59.5 mmole) and toluene (225 mL). The slurry was difficult to stir with a magnetic stir bar. (S)-(−)-α-Methylbenzylamine (Aldrich) (8.1 mL, 62.8 mmole) was added. The flask was equipped with a reflux condenser and a Dean-Stark trap. The mixture was heated at reflux under argon for 3.5 hours and then was cooled to room temperature. The mixture was concentrated on a rotary evaporator to provide 16.52 g (100%) of crude title imide as a white crumbly solid.

The crude title imide was dissolved in boiling ethyl acetate (30 mL) to give a cloudy mixture. The solution was filtered to give 86 mg of a white solid and a clear, pale yellow filtrate. The filtrate was concentrated on a rotary evaporator to a white solid. It was dissolved in boiling ethyl acetate (22 mL). Hexane (56 mL) was added until the solution just became cloudy. The solution was cooled to room temperature without stirring and then was stored in the cold room (∼4° C.) overnight. The crystals were filtered and washed with hexane:ethyl acetate (2.5:1, 3×30 mL) and hexane (3×50 mL) and were dried under house vacuum at room temperature to provide 13.44 g (83%) of a white solid.

The crystals and mother liquor were recombined and dissolved in ethyl acetate (∼200 mL) to give a cloudy white solution. The organic solution was washed with 1N HCl (2×50 mL), saturated aqueous sodium bicarbonate (1×50 mL) and saturated sodium chloride (1×50 mL). The organic layer was dried over magnesium sulfate, filtered and the solvent removed on a rotary evaporator to provide 14.541 g (90%) of crude title imide as an off-white crumbly solid.

The solid was dissolved in boiling ethyl acetate (19 mL). With stirring and heating, hexane (100 mL) was added until white crystals abruptly began falling out of the solution. The solution was cooled to room temperature without stirring. The mixture was stored in the cold room (∼4° C.) for 18 hours. The resulting crystals were filtered, washed with hexane (3×30 mL) and dried under house vacuum at room temperature to provide 13.59 g (84%) of the title imide as shiny white crystals. A second crop (712 mg, 4%) provided additional title imide. The total yield of title imide was 14.302 g (88%).

B.
[1R-[1α,2α(S*),3aα,4α]-3-[[2-(1,3-Dioxolan-2-yl)phenyl]hydroxymethyl]-N-(1-phenylethyl)-2-methylpropyl]-7-oxabicyclo[2.2.1]heptane-2-carboxamide In an oven-dried, argon purged 100 ml flask, 2-(2-bromophenyl)-1,3-dioxolane (16.8 g, 0.0737 mol) was dissolved in THF (30.0 ml). Magnesium turnings (2.1 g, 0.0875 mol) were charged into a separate oven-dried, argon-purged 100 ml 3-necked flask equipped with a condenser. To the magnesium turnings was added a portion (5.0 ml) of the above solution of 2-(2-bromophenyl)-1,3-dioxolane at room temperature. The reaction initiated by itself after stirring for 5 min. The rest of the solution of 2-(2-bromophenyl)-1,3-dioxolane was added into the flask at such a rate which maintained a gentle reflux over a period of 40 min. After all of the solution had been added, the reaction mixture was stirred for another 1.0 hour at room temperature to give the aryl Grignard.

The Part A imide (10.0 g, 0.0369 mol) was added to an oven-dried, argon purged 250 ml 3-necked flask equipped with an addition funnel and a mechanical stirrer. The imide was suspended in THF (14 ml), and cooled in an ice-water bath to 0° C. The Grignard solution of 2-(2-bromophenyl)-1,3-dioxolane prepared above (38.0 ml of a 1.94M solution in THF, 0.0737 mol) was added dropwise over a period of 40 min to this mixture. After the addition was complete, the reaction was stirred at 0° C. for 1.0 h. The ice-water bath was removed and the reaction was stirred for an additional 3.0 h at room temperature. The reaction mixture was cooled to 0° C. with an ice-water bath and quenched by adding ethanol (100 ml). To the resulting mixture was added solid NaBH4 (3.3 g, 0.0873 mol) in 6 equal portions over 20 min. The ice-water bath was allowed to melt and the reaction mixture was allowed to warm to room temperature and stirred for 17 h. The reaction mixture was poured into 10% Na2CO3 (400 ml) and the mixture was extracted with ethyl acetate (3×300 ml). The organic extracts were combined, washed with brine (300 ml), dried over MgSO4, filtered and concentrated in vacuo using a rotary evaporator to obtain the crude title alcohol (22.3 g, 106%) which was used in the next step without any additional purification.

C.
[2S-(2α,3aα,4β,7β,7aα)]-2-(Octahydro-3-oxo-4,7-epoxy-isobenzofuran-1-yl)benzaldehyde The Part B crude alcohol (22.3 g) was dissolved in toluene (50 ml) and heated to reflux for 3.0 h. The resulting solution was cooled to room temperature and then 1N NaOH (150 ml) and ethanol (38 ml) were added. The mixture was vigorously stirred for 4.0 h at room temperature and then was extracted with ethyl acetate (130 ml). The aqueous layer was mixed with THF (26 ml). To this mixture was added 10% HCl (70 ml) at room temperature. The resulting mixture was then stirred at room temperature for 14 h during which time a white precipitate formed. The reaction was cooled to 0° C. for 1.0 hour. The white precipitate was filtered off using a medium fritted glass filter and washed with water (20 ml). The solid was dried under high vacuum to give the title aldehyde as a white solid (7.7 g, 81%) with >99.9% ee as determined by chiral HPLC.

Example 8
[3R-(3α,3aα,4β,7β,7aα)]-3-[2-(1,3-Dioxolan-2-yl)phenyl]hexahydro-4,7-epoxy-1(3H)-isobenzofuranone

A.
[2(1S,2R),3aα,4β,7β,7aα]-Hexahydro-2-(2-hydroxy-1-methyl-2-phenylethyl)-4,7-epoxy-2H-isoindole-1,3-dione A solution of (1S,2R)-(+)-norephedrine (9 g, 59.5 mmole) in tetrahydrofuran (THF) (150 mL) was stirred under argon at room temperature. Oxalic acid (5.4 g, 60.0 mmole) was added as a solid, followed by THF (50 mL). The mixture became thick with a white precipitate and stopped stirring. (3aα,4β,7β,7aα)-Hexahydro-4,7-epoxyisobenzofuran-1,3-dione (Lancaster, 10 g, 59.5 mmole) was added as a solid. Triethylamine (17 mL, 122 mmole) was added. The mixture was heated to reflux at which point it began stirring again. The reaction was heated at reflux for 24 hours.

After cooling to room temperature, the reaction mixture was transferred to a separatory funnel containing saturated sodium bicarbonate (200 mL) and methylene chloride (400 mL). The layers were separated. The aqueous layer was extracted with methylene chloride (1×200 mL). Saturated sodium bicarbonate (100 mL) was added to the aqueous layer. The aqueous layer was extracted with methylene chloride (1×200 mL). The combined organic layers were dried over magnesium sulfate, then filtered and concentrated in vacuo to provide 17.6 g (98%) of the title imide as a yellow oil.

The crude imide was crystallized from hot ethyl acetate/hexane. The stirring was stopped and the mixture was cooled to room temperature and stored in the cold room for three days. The solid was filtered, washed with hexane (3×) and dried in vacuo to produce 14.1 g (79%) of the title imide as an off-white solid.

Analytical Data

TLC: Ethyl acetate:hexane 8:2; $R_f$=0.74; visualization: phosphomolybdic acid $^1$H and $^{13}$C NMR: Consistant. Rotation: $[\alpha]_D$= −40.1° (c=5.32, CH$_3$OH) m.p.: 122°-124° C.

Microanalysis: Cal'd for $C_{17}H_{19}N_1O_4 \cdot 0.07$ mole H$_2$O: C., 67.46; H, 6.38; N, 4.63.

Found: C, 67.64; H, 6.37; N, 4.66.

B.
[3R-(3α,3aα,4β,7β,7aα)]-3-[2-(1,3-Dioxolan-2-yl)phenyl]hexahydro-4,7-epoxy-1(3H)-isobenzofuranone To a solution of Part A imide (604 mg, 2.01 mmol) in tetrahydrofuran (9.0 ml) was added EtMgCl (1.0 ml of a 2.0M solution in tetrahydrofuran, 2.0 mmol) at −78° C. dropwise via a syringe. After the addition was completed, the reaction was stirred for 0.5 hour at −78° C. To this mixture was added dropwise the Grignard solution of 2-(2-bromophenyl)-1,3-dioxolane (2.84 ml of a 1.41M solution in tetrahydrofuran, 4.0 mmol) at −78° C. After the addition was completed, the reaction was stirred at −78° C. for 4.0 h. The dry ice bath was removed and the reaction was stirred for an additional 2.0 h. The reaction mixture was cooled to 0° C. with an ice-water bath and quenched by adding ethanol (15 ml). To the resulting mixture was added solid NaBH$_4$ (300 mg, 7.9 mmol). The ice-water bath was allowed to melt and the reaction mixture was allowed to warm to room temperature and stirred for 14 h. The reaction mixture was poured into 10% Na$_2$CO$_3$ (20 ml) and the mixture was extracted with ethyl acetate (3×50 ml). The organic extracts were combined, dried over MgSO$_4$, filtered and concentrated in vacuo to obtain the crude benzylic alcohol (1.22 g, 104%) which was used in the next step without any additional purification.

The above crude benzylic alcohol (1.22 g) was dissolved in toluene (20 ml) and heated to reflux for 3.0 h. The resulting solution was cooled to room temperature and then concentrated in vacuo to give the crude lactone acetal. Purification of the crude product on flash silica gel (1×10 cm, hexane first followed by 20% ethyl acetate/hexane as eluant) gave the title lactone acetal as a colorless oil which solidified upon standing at room temperature (553 mg, 91%) with 96% ee as determined by chiral HPLC.

The title lactone acetal is then treated with base such as NaOH in the presence of an alcohol solvent such as ethanol to form a salt which is treated with strong acid such as HCl to form the aldehyde intermediate as described in Example 1.

Example 9
[3R-(3α,3aα,4β,7β,7aα)]-3-[2-(1,3-Dioxolan-2-yl)phenyl]-hexahydro-4,7-epoxy-1(3H)-isobenzofuranone

A.
[2(R),3aα,4β,7β,7aα]-Octahydro-1,3-dioxo-N-pentyl-α-(hydroxymethyl)-4,7-epoxy-2H-isoindole-2-acetamide In an argon purged 1L 3-necked flask, fitted with a reflux condenser, was placed 28.0 g of (3aα,4β,7β,7aα)-hexahydro-4,7-epoxyisobenzofuran-1,3-dione, 45 g of Example 5 amine and 575 mL of tetrahydrofuran (THF). To the stirred suspension was added 50 mL of triethylamine. The mixture was heated to reflux for 6 hours. The mixture was then allowed to cool to room temperature. The mixture was poured into saturated sodium bicarbonate (2 L) and extracted with methylene chloride (3×1 L, 500 mL). The combined organic layers were dried over magnesium sulfate, filtered and concentrated in vacuo to provide the crude title imide.

The crude title imide was dissolved in 300 mL of hot ethyl acetate. Hexane (520 mL) was added slowly, while maintaining reflux. After addition of the hexane was complete, heating was discontinued and the mixture was allowed to cool to room temperature. The resulting crystals were collected by suction filtration to provide 41.4 g (77%) of the title imide. A second crop was obtained from the mother liquor to provide an additional 7.33 g (14%) of the title imide.

Analytical Data

TLC; Ethyl actate: hexane 7:3, $R_f$=0.13; visualization: phosphomolybdic acid.

Microanalysis: Cal'd for $C_{16}H_{24}N_2O_5$: C, 59.24; H, 7.46; N, 8.64.

Found: C, 59.34; H, 7.56; N, 8.72

B. [3R-(3α,3aα,4β,7β,7aα)]-3-[2-(1,3-Dioxolan-2 -yl)phenyl]hexahydro-4,7-epoxy -1(3H)-isobenzofuranone To a solution of Part A imide (602 mg, 2.00 mmol) in tetrahydrofuran (8.0 ml) was added EtMgCl (2.0 ml of 2.0M solution in tetrahydrofuran, 4.0 mmol) at 0° C. dropwise via a syringe. After the addition was completed, the reaction was stirred for 0.5 hour at room temperature. The mixture was cooled to 0° C. and to this mixture was added dropwise the Grignard solution of 2-(2-bromophenyl)-1,3-dioxolane (2.7 ml of a 1,096M solution in tetrahydrofuran, 2.96 mmol). After the addition was completed, the reaction was stirred at 0° C. for 1.0 h. The reaction was quenched by adding ethanol (8 ml). To the resulting mixture was added solid NaBH$_4$ (400 mg, 10.5 mmol). The reaction mixture was stirred for 2 h at room temperature. The reaction mixture was poured into 10% Na$_2$CO$_3$ (30 ml) and the mixture was extracted with ethyl acetate (2×40 ml). The organic extracts were combined, dried over MgSO$_4$, filtered and concentrated in vacuo to obtain the crude benzylic alcohol which was used in the next step without any additional purification.

The above crude benzylic alcohol was dissolved in toluene (20 ml) and heated to reflux for 3.0 h. The resulting solution was cooled to room temperature and then concentrated in vacuo to give the crude lactone acetal. Purification of the crude product on flash silica gel (1×10 cm, hexane first followed by 20% ethyl acetate/hexane as eluant) gave the pure lactone acetal as a colorless oil which solidified upon standing at room temperature (324 mg, 53%) with 61.6% ee as determined by chiral HPLC.

The title lactone acetal may be employed to form the Example 1 aldehyde employing procedures described in Example 1.

Example 10

[3R-(3α,3aα,4β,7β,7aα)]-3-[2-(1,3-Dioxolan-2-yl)phenyl]hexahydro-4,7-epoxy-1(3H)-isobenzofuranone

A.

[2(R),3aα,4β,7β,7aα]-Octahydro-1,3-dioxo-N-pentyl-α-[[(tributylsilyl)oxy]-methyl]-4,7-epoxy-2H-isoindole-2-acetamide In a 500 mL flask was placed 10.0 g of the Example 9, Part A imide, 250 mL of dimethylformamide (DMF, anhydrous), 2.31 g of imidazole and 5.11 g of tert-butyldimethylsilyl chloride (TBS-Cl). The mixture was stirred at room temperature for 17 hours, then diluted with diethyl ether (500 mL) and washed with sat'd sodium bicarbonate (300 mL), water (4×400 mL) and brine (300 mL). The organic layer was dried over magnesium sulfate, filtered and concentrated in vacuo to provide 12.3 g (91%) of the title TBS-protected imide.

Analytical Data

TLC: Ethyl acetate:hexanes 3:2; $R_f$=0.6; visualization: phophomolybdic acid.

B.

[3R-(3α,3aα,4β,7β,7aα)]-3-[2-(1,3-Dioxolan-2-yl)-phenyl]hexahydro-4,7-epoxy -1(3H)-isobenzofuranone To a solution of the Part A imide (410 mg, 1.0 mmol) in tetrahydrofuran (2.0 ml) was added EtMgCl (0.5 ml of 2.0M solution in tetrahydrofuran, 1.0 mmol) at 0° C. dropwise via a syringe. After the addition was completed, the reaction was stirred for 0.5 hour at 0° C. To this mixture was added dropwise the Grignard solution of 2-(2-bromophenyl)-1,3-dioxolane (1.7 ml of a 1.2M solution in 50% tetrahydrofuran/toluene, 2.04 mmol). After the addition was completed, the reaction was stirred at 0° C. for 1.0 h. The reaction mixture was stirred for an additional 2.0 h at room temperature. The reaction mixture was cooled to 0° C. and additional Grignard solution of 2-(2-bromophenyl)-1,3-dioxolane (1.5 ml of a 0.73M solution in tetrahydrofuran, 1.10 mmol) was added. The reaction mixture was stirred for 10 min at 0° C. and then for 1.0 h at room temperature. The reaction was quenched by adding ethanol (8 ml). To the resulting mixture was added solid NaBH$_4$ (200 mg, 5.2 mmol). The reaction mixture was stirred for 14 h at room temperature. The reaction mixture was poured into 10% Na$_2$CO$_3$ (15 ml) and the mixture was extracted with ethyl acetate (2×20 ml). The organic extracts were combined, dried over MgSO$_4$, filtered and concentrated in vacuo to obtain the crude benzylic alcohol which was used in the next step without any additional purification.

The above crude benzylic alcohol was dissolved in toluene (10 ml) and heated to reflux for 3.0 h. The resulting solution was cooled to room temperature and then concentrated in vacuo to give the crude title lactone acetal. Purification of the crude product on flash silica gel (1×10 cm, 15% ethyl acetate/hexane as eluant) gave the title lactone acetal as a colorless oil which solidifies upon standing at room temperature (110 mg, 35%) with 86% ee as determined by chiral HPLC.

The title lactone acetal may be employed to form the Example 1 aldehyde employing procedures described herein.

Example 11

[2(1S,2R),3aα,4β,7β,7aα]-Hexahydro-2-(2-hydroxy-1,2-diphenylethyl) -4,7 -epoxy-2H-isoindole-1,3-dione A solution of (1R,2S)-(-)-2-Amino-1,2-diphenylethanol (6.3 g, 29.5 mmole) in tetrahydrofuran (THF) (75 mL) was stirred under argon at room temperature. Oxalic acid (2.7 g, 30.0 mmole) was added as a solid, followed by THF (25 mL). The mixture became thick with white precipitate and stopped stirring. (3aα,4β,7β,7aα)-Hexahydro-4,7-epoxyisobenzofuran-1,3-dione (Lancaster, 5 g, 29.7 mmole) was added as a solid. Triethylamine (8.3 mL, 59.5 mmole) was added. The mixture was heated to reflux at which point it began stirring again. The reaction refluxed for 22 hours.

After cooling to room temperature, the reaction mixture was transferred to a separatory funnel containing saturated sodium bicarbonate (100 mL) and methylene chloride (200 mL). The layers were separated. The aqueous layer was extracted with methylene chloride (2×200 mL). The combined organic layers were dried over magnesium sulfate, then filtered and concentrated in vacuo to provide 12.4 g (116%) of the title compound as a pale yellow foam.

The crude title compound was crystallized from hot ethyl acetate/hexane. The stirring was stopped and the mixture was cooled to room temperature, and stored in the cold room overnight. The solid was filtered, washed with hexane (3 times) and dried in vacuo to produce 8.14 g (76%) of the title compound as a white solid.

Analytical Data

TLC: Ethyl acetate:hexane 8:2; $R_f$=0.81.; visualization: phosphomolybdic acid Rotation: $[\alpha]_D$= +43.7° (c=2.59, $CH_3OH$) m.p.: 174°–176° C.

Following the procedure of Example 1, Parts B and C, the title imide may be employed to form the Example 1 aldehyde intermediate.

Example 12

[2(S),3aα,4β,7β,7aα]-Hexahydro-2-[1-(hydroxymethyl)-2-methylpropyl]-4,7-epoxy-2H-isoindole-1,3-dione A solution of (S)-(+)-2-amino-3-methyl-1-butanol (6.2 g, 60.1 mmole) in THF (150 mL) was stirred under argon at room temperature. Oxalic acid (5.36 g, 60.0 mmole) was added as a solid, followed by tetrahydrofuran (THF) (50 mL). The mixture became thick with white precipitate and stopped stirring. (3aα,4β,7β,7aα]-Hexahydro-4,7-epoxyisobenzofuran-1,3-dione (Lancaster, 10 g, 59.5 mmole) was added as a solid. Triethylamine (17 mL, 122 mmole) was added. The mixture was heated to reflux at which point it began stirring again. The reaction refluxed for 23 hours.

After cooling to room temperature, the reaction mixture was transferred to a separatory funnel containing saturated sodium bicarbonate (300 mL) and methylene chloride (600 mL). The layers were separated. The aqueous layer was extracted with methylene chloride (1×300 mL and 1×200 mL). The combined organic layers were dried over magnesium sulfate, then filtered and concentrated in vacuo to provide 9.8 g (65%) of the title compound as a pale yellow solid.

The crude title compound was taken up in hot ethyl acetate (10 mL). Hexane (6 mL) was added with stirring until solids abruptly began to come out. The stirring was stopped. The mixture was cooled to room temperature and stored in the cold room for 16 hours. The solid was filtered, washed with hexane (3×) and dried in vacuo to produce 5.8 g (39%) of the title compound as a pale yellow solid. A second crop afforded 2.97 g (20%) of the title compound as a white solid.

Analytical Data

TLC: Ethyl acetate:hexane 8:2; $R_f$=0.46; visualization: phosphomolybdic acid Rotation: $[\alpha]_D$= +6.30° (C=5.05, $CH_3OH$) m.p.: 102°–103° C.

Microanalysis: Cal'd for $C_{13}H_{19}N_1O_4 \cdot 0.10$ mole EtOAc: C, 61.36; H, 7.62; N, 5.34.

Found: C, 61.46; H, 7.57; N, 4.97.

K.F. Found: 0.09.

The title imide may be employed to form the Example 1 benzaldehyde using procedures described herein.

Example 13

[2(S),3aα,4β,7β,7aα]-Hexahydro-2-[1-(hydroxymethyl)-2-phenylethyl]-4,7-epoxy-2H-isoindole-1,3-dione A solution of (S)-(−)-2-amino-3-phenyl-1-propanol (9 g, 59.5 mmole) in tetrahydrofuran (THF) (150 mL) was stirred under argon at room temperature. Oxalic acid (5.36 g, 59.5 mmole) was added as a solid, followed by THF (50 mL). The mixture became thick with white precipitate and stopped stirring. (3aα,4β,7β,7aα]-Hexahydro-4,7-epoxyisobenzofuran-1,3-dione (Lancaster, 10 g, 59.5 mmole) was added as a solid. Triethylamine (17 mL, 122 mmole) was added. The mixture was heated to reflux at which point it began stirring again. The reaction refluxed for 22 hours.

After cooling to room temperature, the reaction mixture was transferred to a separatory funnel containing saturated sodium bicarbonate (200 mL) and methylene chloride (400 mL). The layers were separated. Saturated sodium bicarbonate (100 mL) and methylene chloride (100 mL) were added to the aqueous layer. The contents of the separatory funnel were filtered through a coarse glass frit. A cake of white solid was collected on the frit and discarded The filtrate was separated without problem. The aqueous layer was extracted with methylene chloride (1×100 mL). The combined organic layers were dried over magnesium sulfate, then filtered and concentrated in vacuo to provide 12.3 g (68%) of the title compound as a yellow solid.

The crude title compound was taken up in hot ethyl acetate (250 mL) and then cooled. The resulting solid was filtered off. The filtrate was concentrated, then dissolved in hot ethyl acetate (45 mL). Hexane (90 mL) was added with stirring until the solution turned cloudy. The stirring was stopped and the mixture was cooled to room temperature. The solid was filtered, washed with hexane (3×30 mL) and dried in vacuo to produce 9.89 g (55%) of the title compound as a pale yellow solid.

Analytical Data

TLC: Ethyl acetate:hexane 8:2; $R_f$=0.41; visualization: phosphomolybdic acid Rotation: $[\alpha]_D$=67.8° (c=5.70, $CH_3OH$) m.p.: 129°–131° C.

Microanalysis: Cal'd for $C_{17}H_{19}N_1O_4$: C, 67.76; H, 6.35; N, 4.65.

Found: C, 67.72; H, 6.32; N, 4.66.

K.F. Found: 0.00

The title imide may be employed to form the Example 1 aldehyde using procedures described herein.

Example 14

[3R-(3α,3aα,4β,7β,7aα)]-3-[2-(1,3-Dioxolan-2-yl)phenyl]hexahydro-4,7-epoxy-1(3H)-isobenzofuranone

A.

[2(S),3aα,4β,7β,7aα]-Hexahydro-2-(2-hydroxy-1-phenylethyl)-4,7-epoxy-2H-isoindole-1,3-dione A solution of (R)-(−)-2-phenylglycinol (4 g, 29.2 mole) in tetrahydrofuran (THF) (75 mL) was stirred under argon at room temperature. Oxalic acid (2.6 g, 28.9 mole) was added as a solid, followed by THF (25 mL). The mixture became thick with white precipitate and stopped stirring. (3aα,4β,7β,7aα]-Hexahydro-4,7-epoxyisobenzofuran-1,3-dione (Lancaster, 4.9 g, 29.1 mole) was added as a solid. Triethylamine (8 mL, 57.4 mole) was added. The mixture was heated to reflux at which point it began stirring again. The reaction was refluxed for 18 hours.

After cooling to room temperature, the reaction mixture was transferred to a separatory funnel containing saturated sodium bicarbonate (100 mL) and methylene chloride (200 mL). The layers were separated. Saturated sodium bicarbonate (100 mL) and methylene chloride (100 mL) were added to the aqueous layer and separated with difficulty. The aqueous layer was extracted with methylene chloride (1×100 mL) with difficulty. The combined organic layers were dried over magnesium sulfate, then filtered and concentrated in vacuo to provide 8.54 g (100%) of the title imide as a yellow foam.

The crude title imide was dissolved in EtOAc (45 mL) and heated to reflux. Hexane (45 mL) was added with stirring until the solution just turned cloudy. The stirring was stopped and the mixture was cooled to room temperature. The solid was filtered, washed with 3:1 hexane:ethyl acetate (3×30 mL) and dried in vacuo to produce 6.42 g (77%) of the title imide as a pale yellow solid.

Analytical Data

TLC: Ethyl acetate: hexane 8:2; $R_f$=0.39; visualization: phosphomolybdic acid Rotation: $[\alpha]_D$=0.409° (C=6.60, CH$_3$OH) m.p.: 121°–123° C.

Microanalysis: Cal'd for $C_{16}H_{17}N_1O_4$: C, 66.89; H, 5.96; N, 4.88.

Found: C, 66.7; H, 5.94; N, 4.97

B.
[3R-(3α,3aα,4β,7β,7aα)]-3-[2-(1,3-Dioxolan-2-yl)phenyl]hexahydro-4,7-epoxy-1(3H)-isobenzofuranone In a 25 mL flame-dried, 2-necked flask, fitted with a reflux condenser, was placed 0.0802 g of magnesium metal and 11.5 mL of tetrahydrofuran and a crystal of I$_2$. To the warmed solution was added 0.6545 g of 2-(2-bromophenyl)-1,3-dioxolane. The mixture was heated to reflux and a second crystal of I$_2$ and 20 μL of 1,2-dibromoethane were added. Grignard formation commenced immediately. After 40 minutes at reflux, the formation of the Grignard reagent appeared to be complete. The solution was allowed to cool to room temperature.

In a separate, flame-dried 25 mL flask was placed 0.2946 g of the Part A imide, and 3.0 mL of tetrahydrofuran. The mixture was cooled in a −78° C. bath and the Grignard reagent prepared above was added via syringe at such a rate that the internal temperature never rose above −70° C. After the addition was complete, the mixture was allowed to warm to room temperature over 5 hours. The mixture was poured into saturated sodium bicarbonate (60 mL) and extracted with methylene chloride (2×60 mL). The combined organic layers were dried over magnesium sulfate, filtered and concentrated in vacuo to provide 0.5950 g of crude addition product, which was carried on without purification.

The crude product was placed in a 25 mL flask with 2 mL of tetrahydrofuran and 2 mL of ethanol. To the stirred solution was added 0.0789 g of sodium borohydride. The mixture was stirred at room temperature for 1 hour, then poured into saturated sodium bicarbonate (60 mL) and extracted with methylene chloride (2×60 mL). The combined organic layers were dried over magnesium sulfate, filtered and concentrated in vacuo to provide 0.6 g of crude benzylic alcohol, which was carried on without purification.

The crude benzylic alcohol was placed in a 25 mL flask with 10.5 mL of toluene. The flask was fitted with a reflux condenser and the mixture was heated to reflux for 5 hours, then at 100° C. for 18 hours. The mixture was allowed to cool to room temperature, then loaded directly onto a silica gel column (30×230 mm) and eluted with 2:3 ethyl acetate:hexanes (1 L) followed by 3:2 ethyl acetate:hexanes (1 L) to provide 0.17 g (63%) of the desired title lactone-acetal.

Analytical Data

TLC: Ethyl acetate:hexane 2:3; $R_f$=0.55; visualization: p-Anisaldehyde stain. Rotation: $[\alpha]_D$= +40.2° (c=0.56, CH$_3$OH)

The title lactone acetal may be employed to form the Example 1 aldehyde employing procedures described herein.

The following Table A shows the ratio of desired to undesired enantiomers of the lactone acetal obtained from various imides and the Grignard reagant prepared from 2-(2-bromophenyl)-1,3-dioxolane or the aryl lithium reagent prepared from 2-(2-bromophenyl)-1,3-dioxolane.

TABLE A

Selection of an Aryl Nucleophile/Imide Combination

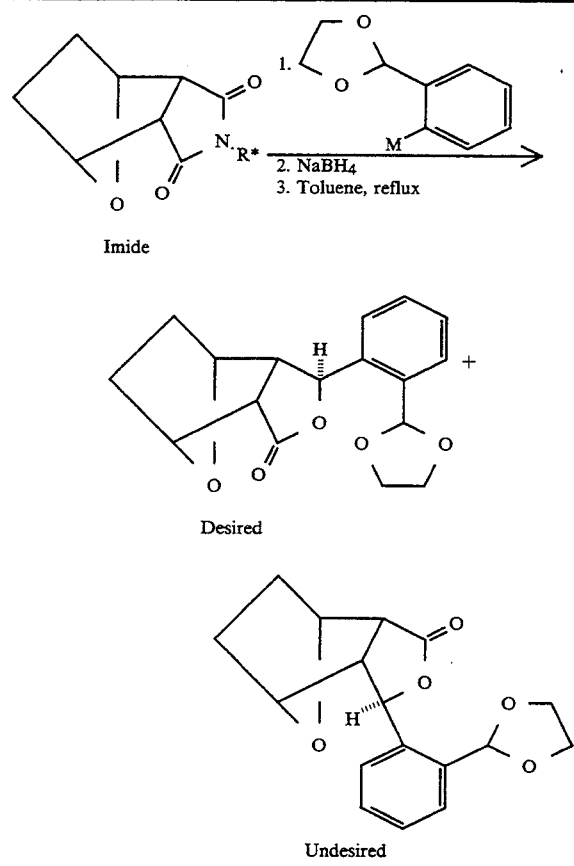

| Ex. No. | R* (config) | ArM (eq) | % Yield | Ratio of Enantiomers[1] |
|---|---|---|---|---|
| 15 | Norephedrine (1S, 2R) | ArMgBr (2.51) | 41% | 28:72 |
| 16 | Norephedrine (1S, 2R) | ArLi (2.51) | 59% | 38:62 |
| 17 | Phenylglycinol (R) | ArMgBr (2.78) | 63% | 13:87 |
| 18 | Phenylglycinol (R) | ArLi (2.52) | 29% | 25:75 |
| 19 | Valinol (S) | ArMgBr (2.77) | 65% | 86:14 |

[1]Ratios are expressed as the ratio of desired to undesired Lactone-Acetal.

Wittig-Horner Olefination was studied as a means to convert the aldehyde of Example 1 to Unsaturated Ester (Example 3A). The results of this study are shown in Table B below.

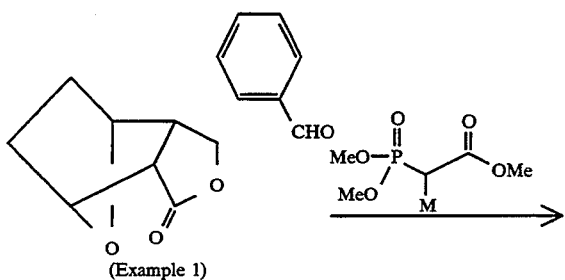

(Example 1)

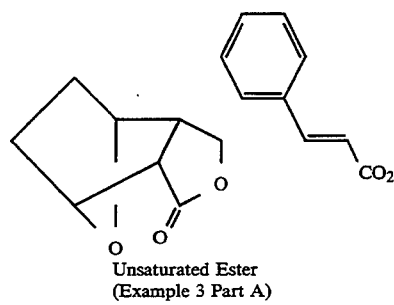

Unsaturated Ester
(Example 3 Part A)

through Celite and washed with n-BuOAc (4×10 ml) directly into a 1-L distillation flask.

The filtrate was partially distilled through a short path still with a heating mantle equipped with a thermocouple. Enough heat (mantel temp. 165°) was applied to distill out 250 ml distillate (furan and TEA) at bp 88°-122° over 30 min. The mantle temperature (thermocouple) was maintained at ~155° so that another 140 ml distillate came over at ~124° over 1.5 hrs. TLC (silica gel, EtOAc/HOAc/MeOH 8:1:1, visualized by ceric ammonium molybdate) showed disappearance of acid amides with 2 spots at $R_f$ 0.28 and 0.34 and title compound at $R_f$ 0.85. After cooling to room temperature, the residue in the pot (~400 ml) was washed into a 1-L separatory funnel with EtOAc and washed with 1N HCl (300 ml). During the washing, a voluminous precipitate formed. It was redissolved by adding EtOAc (300 ml). The aqueous layer was separated and the organic layer was washed with water (300 ml), 5% NaHCO$_3$ (300 ml), brine (100 ml), and dried (MgSO$_4$). Darco G-60 (14 g) was added and stirred for 15 min, filtered through Celite, and washed with EtOAc (4×10 ml). The filtrate was evaporated at a bath temperature of 50° until the residue weighed 300 g. The residue was heated on the steam bath while slowly adding heptane (950 ml).

TABLE B

Wittig-Horner Olefination of Example 1 aldehyde.

| Ex. No. | Solvent | Phosphonate (eq.) | Base | Temperature | trans: cis | Crude Yield |
|---|---|---|---|---|---|---|
| 20 | THF | 1.10 | LiHMDS | −78° C. to r.t. | 8:1 | 110% |
| 21 | THF | 1.10 | NaH | −78° C. to r.t. | 14:1 | 107% |
| 22 | THF | 1.10 | KOC(CH$_3$)$_2$-CH$_2$CH$_3$ | −78° C. to r.t. | 26:1 | 95% |
| 23 | THF | 1.10 | KOC(CH$_3$)$_2$-CH$_2$CH$_3$ | 0° C. to r.t. | 19:1 | 96% |
| 24 | THF | 1.02 | KOC(CH$_3$)$_2$-CH$_2$CH$_3$ | −78° C. to r.t. | 18:1 | 91% |
| 25 | CH$_3$CN | 1.05 | LiCl/DBU | r.t. | 36:1 | 101% |

Example 26

[2(S),3aα,4β,7β,7aα,]-Hexahydro-2-(1-phenylethyl)-4,7-epoxy-1H-isoindole-1.3(2H)-dione Furan (222 ml, 3.06M) was added under Ar to maleic anhydride (50.0 g, 0.510M) that had been broken up into small pieces in a 2-L 3-necked flask (dried at 125°) equipped with a mechanical stirrer and chilled in a cold water bath. After the addition, the flask was stoppered and the maleic anhydride was dissolved by stirring. The solution was let stand for 22 hrs without stirring. A crystalline mass formed.

n-BuOAc (500 ml) was added under Ar to form a suspension. The mixture was chilled in an ice-bath. A mixture of triethylamine (TEA) (71.1 ml, 0.510M), and (S)-(−)-α-methylbenzylamine (65.7 ml, 0.510M) was added dropwise over 15 min so that the temperature of the reaction mixture never rose above 10°. The suspension dissolved after stirring for 10 min, the ice-bath was removed and 5% Pd/C (7.19 g) was added. H$_2$ was sparged through the mixture. The hydrogenation was followed by TLC (silica gel, EtOAc/HOAc/MeOH 8:1:1, visualized by KMnO$_4$ spray). After 2.5 hrs, $^1$H NMR (CDCl$_3$, 1 drop of the reaction mixture filtered and washed with CDCl$_3$ through Celite into the NMR tube) showed no olefin. The excess H$_2$ was removed by sparging with N$_2$ for 15 min. The catalyst was filtered Crystals started to form immediately. The hot mixture was allowed to cool to room temperature and let stand for 6 hrs. The crystals were collected on a filter (25–50 μ) with their own mother liquor, washed with cold heptane, and dried overnight at room temperature. The white crystals of title compound weighed 117.64 g (85%), mp. 108°-9°, [α]$_D$−67° [c=5.08, CHCl$_3$]. The so-formed imide was used to prepare aldehyde as described in Example 1.

Example 27

[2(S),3aα,4β,7β,7aα]-Hexahydro-2-(1-phenylethyl)-4,7-epoxy-1H-isoindole-1.3(2H)-dione A. (S)-(−)-α-Methylbenzylmaleamic acid

| Material | F.W. | Moles | Equiv. | Amount |
|---|---|---|---|---|
| Maleic Anhydride | 98.06 | 0.102 | 1.0 | 10.00 g |
| MBA* | 121.18 | 0.107 | 1.05 | 13.80 mls |
| Acetonitrile | — | — | — | 100.0 mls |

*(S)-(−)-α-methylbenzylamine

A 250 mL three-necked flask fitted with mechanical stirrer, condenser and thermocouple was charged with maleic anhydride and acetonitrile.

The (S)-(−)-α-methylbenzylamine was added dropwise via an addition funnel (over a fifteen minute period) with stirring to the maleic anhydride solution. The reaction to form the title compound was complete in three hours according to HPLC.

B. N-(S)-(−)-α-Methylbenzylmaleimide

| Material | F.W. | Moles | Equiv. | Amount |
| --- | --- | --- | --- | --- |
| Part A maleamic acid | — | | 1.0 | 100.0 mls approx. |
| Diisopropylamine | 101.19 | 0.204 | 2.0 | 28.58 mls |
| HMDS* | 161.14 | 0.204 | 2.0 | 43.00 mls |

*1,1,1,3,3,3-Hexamethyldisilazane

Diisopropylamine was added to the stirring colorless reaction solution via an addition funnel followed by a rapid addition of the HMDS.

The reaction solution was heated to reflux (76.0° C.) and refluxing was maintained for 18 hours. The reaction solution changed from a colorless solution to a dark wine solution. The reaction to form the title compound was judged complete via HPLC.

The reaction solution was allowed to cool to room temperature and the acetonitrile was removed in vacuo giving a wine colored oil. Ethanol (50 ml) and 1N HCl (50 ml) were added to the oil and the solution was stirred at 45° C. for ten minutes. The ethanol was removed in vacuo and the wine solution was extracted with methylene chloride (100 ml). The organic layer was washed with saturated sodium bicarbonate (50 ml), brine (50 ml) and dried over anhydrous magnesium sulfate. The methylene chloride was removed in vacuo to give a dark wine oil (13.09 g, 63.8M % yield). This oil was purified on a pad of silica gel eluting with hexane/ethyl acetate 7:3 to give the title compound as a pale amber oil (10.71 g, 52.2M % yield).

C.
[2(S),3aα,4β,7β,7aα]-Hexahydro-2-(1-phenylethyl)-4,7-epoxy-1H-isoindole-1,3(2H)-dione AlCl₃ (0.199 g, 1.49 mM) was added to Part B imide (1.0 g, 4.98 mM) and furan (1.08 ml, 14.9 mM) stirred in CH₂Cl₂ (16.6 ml) chilled in an ice-bath under an argon atmosphere. After 15 min the ice-bath was removed and the mixture was stirred overnight at room temperature. A black precipitate was formed. TLC (silica gel, EtOAc-Hexane 1:1, visualized by UV and ceric ammonium molybdate) showed disappearance of the imide $R_f$ 0.71 and appearance of the product at $R_f$ 0.44. EtOAc (20 ml) and 1N HCl (20 ml) were added and stirred for 10 min. The mixture was filtered through Celite to remove a brown solid which was washed on the filter with EtOAc (100 ml). The filtrate was added to a separatory funnel, the aqueous layer separated, and the organic layer washed with 1N HCl (20 ml), water (20 ml), 5% NaHCO₃ (20 ml), brine (10 ml), and dried (MgSO₄ for 5 min). Darco G-60 (0.5 g) was added and stirred for 30 min. The mixture was filtered through Celite and evaporated to ~25 ml. The residue was washed with 25 ml EtOAc into a hydrogenation flask containing 5% Pd/C (0.1 g). H₂ was sparged through the mixture for 1 hr. N₂ was sparged for 15 min. to remove excess H₂. Darco G-60 (0.5 g) was added and stirred for 30 min. The mixture was filtered through Celite, washed with EtOAc, and evaporated to give 1.27 g (94% crude yield).

The semisolid residue was dissolved in EtOAc (1.5 ml) and heptane (10 ml) by heating on the steam bath. The solution was let stand at room temperature for 2 hrs and at 0° for 3 hrs. The crystals were filtered, washed with cold hexane and dried overnight under vacuum to yield 1.12 g (83%) of the title compound, mp. 107°–9°.

Anal. calcd. for C₁₆H₁₇NO₃ (271.3) C, 70.83; H, 6.32; N, 5.16; H₂O 0.00

Found: C, 70.88; H, 6.25; N, 5.19; H₂O 0.01 (KF)

The title intermediate was employed to prepare the aldehyde as described in Example 1.

Example 28

[2(S),3aα,4β,7β,7aα]-3a,4,7,7a-Tetrahydro-2-(1-phenylethyl) -4.7-epoxy-1H-isoindole-1,3(2H)-dione AlCl₃ (0.199 g, 1.49 mM) was added to a solution of imide (prepared as described in Example 27, Part B) (1.0 g, 4.98 mM) and furan (1.08 ml, 14.9 mM) in CH₂Cl₂ (16.6 ml) chilled in an ice-bath under an argon atmosphere. After stirring for 15 min. the ice-bath was removed and the mixture stirred overnight at room temperature. A black precipitate was formed. TLC (silica gel, EtOAc-hexane 1:1, visualized by UV and ceric ammonium molybdate) showed disappearance of Example 27 Part B imide ($R_f$ 0.71) and appearance of the title compound at $R_f$ 0.44. EtOAc (20 ml) and 1N HCl (20 ml) were added and stirred for 10 min. The mixture was filtered through Celite from a brown solid which was washed on the filter with EtOAc (100 ml). The organic layer was washed with 1N HCl (20 ml), water (20 ml), 5% NaHCO₃ (20 ml), brine (10 ml), and dried (MgSO₄ for 5 min). Darco G-60 (0.5 g) was added and stirred for 30 min. The mixture was filtered through Celite and evaporated to a foam which solidified to give 1.36 g (99% crude yield estimated from NMR, contained 10% EtOAc).

The crude product was dissolved in 10% EtOAc/hexane and filtered through a pad of silica gel and then chromatographed on silica gel (25×300 mm column). Product was eluted with EtOAc/hexane (1:4) collecting 50 ml fractions. Pure fractions by TLC (silica gel, EtOAc/hexane 1:1, visualized by UV and ceric ammonium molybdate, $R_f$ 0.44) were collected and evaporated to yield 1.18 g (88%) of the title compound, top. 101°–3°, $[\alpha]_D = -70.0°$ (c=1.5, CHCl₃).

Anal. calcd. for C₁₆H₁₅NO₃ (269.3) C, 71.36; H, 5.61; N, 5.20; H₂O 0.00

Found: C, 71.26; H, 5.61: N, 5.24; H₂O 0.02 (KF)

The title imide was hydrogenated to the corresponding hexahydro compound as described in Example 27 and employed to prepare aldehyde as described in Example 1.

Example 29

(S)-(−)-α-Methylbenzylmaleimide

| Material | F.W. | Moles | Equiv. | Amount |
| --- | --- | --- | --- | --- |
| Maleamic acid* | 219.24 | 0.245 | 1.0 | 53.8 g |
| HMDS** | 161.40 | 0.758 | 3.1 | 160.0 ml |
| Acetonitrile | — | — | — | 1500 ml |

*(S)-(−)-α-Methylbenzylmaleamic acid
**1,1,1,3,3,3-Hexamethyldisilazane

A 2000 mL three necked flask fitted with mechanical stirrer, condenser and thermocouple was charged with 53.8 grams of Example 27 Part A maleamic acid, 1500 mls. of acetonitrile and 160 mls. of HMDS.

The above solution was refluxed for 48 hours. The reaction was judged to be complete by the absence of starting maleamic acid by HPLC.

The pink reaction solution was cooled to room temperature and acetonitrile was removed in vacuo. The resulting oil was dissolved in ethyl acetate (500 mls) and washed with 50 mls. of a 1N HCl solution followed by 100 mls. of a saturated bicarbonate solution. The rich organic layer was washed with a saturated brine solution and dried over magnesium sulfate. The removal of the ethyl acetate in vacuo afforded 36.0 grams of title compound. 72.9M % yield.

The reaction solution was allowed to cool to room temperature and the acetonitrile was removed in vacuo giving a wine colored oil. Ethanol (50 ml) and 1N HCl (50 ml) were added to the oil and the solution was stirred at 45° C. for ten minutes. The ethanol was removed in vacuo and the wine solution was extracted with methylene chloride (100 ml). The organic layer was washed with saturated sodium bicarbonate (50 ml), brine (50 ml) and dried over anhydrous magnesium sulfate. The methylene chloride was removed in vacuo to give a dark wine oil (13.09 g, 63.8M % yield). This oil was purified on a pad of silica gel eluting with hexane/ethyl acetate 7:3 to give the title compound as a pale amber oil (10.71 g, 52.2M % yield).

The title compound was employed to prepare the Examples 27 and 28 compounds.

Example 30

[2S-(2α,3α,4β,7β,7aα)]-2-(Octahydro-3-oxo-4,7-epoxyisobenzofuran-1-yl)-benzaldehyde A.
(S)-1-[2-(Acetyloxy)-1-phenylethyl]-2,5-dihydro-1H-pyrrol-2,5-dione

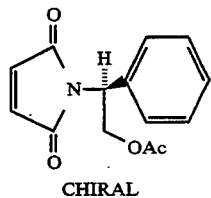

CHIRAL 1,3-Bis(trimethylsilyl)urea (0.745 g, 3.65 mM) was added to (S)-(+)-2-phenylglycinol (0.5 g, 3.65 mM) dissolved in THF (10 ml, distilled from Na/benzophenone). The mixture was refluxed for 1 hr. A precipitate formed. Maleic anhydride (0.376 g, 3.83 mM) was added and the mixture was refluxed for 0.5 hr. H₂O (66 μl, 3.65 mM) was added to the cooled mixture and stirred for 30 min. to form the intermediate

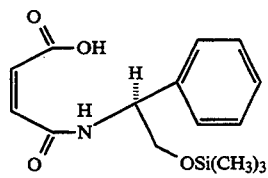

which was not recovered from the reaction mixture. Tetrabutyl-ammonium fluoride (TBAF.3H₂O, 0.115 g, 0.365 mM), acetic anhydride (Ac₂O) (3.44 ml, 36.5 mM), and TEA (3.0 ml, 21.9 mM) were added and the mixture refluxed for 2.5 hrs. After cooling to room temperature, H₂O (15 ml) was added and stirred for 1 hr. The reaction mixture was taken up in EtOAc (75 ml), washed with water (2×50 ml), 5% NaHCO₃ (50 ml), brine (25 ml), dried (MgSO₄), and evaporated to a black oil: 0.88 g. The oil was Kugalrohr distilled under vacuum (~0.3 mm), oven temperature 110°-30°, giving the title compound as a colorless oil: 0.79 g (83% yield). TLC (silica gel, EtOAc/hexane 7:3 visualized with UV and KMnO₄) showed the product as one spot at R$_f$0.60.

Calcd. for $C_{14}H_{13}NO_4$ (259.26) C, 64.86; H, 5.05; N, 5.40

Found: C, 65.15; H, 5.05; N, 5.31; H₂O 0.00 (KF)

B.
[2(S),3aα,4β,7β,7aα]-2-[2-(Acetyloxy)-1-phenylethyl]-3a,4,7,7a-tetrahydro-4,7-epoxy -1H-isoindole-1,3(2H) -dione

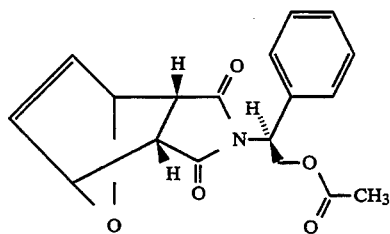

Tin chloride (2.90 ml, 2.90 mM, 1.0M in CH₂Cl₂) was added by syringe to 10 ml CH₂Cl₂ at room temperature under argon. Part A compound (0.5 g, 1.93 mM) in 1 ml CH₂Cl₂ was added and then furan (0.70 ml, 9.65 mM) was introduced. After 6 hours another 0.70 ml furan was added and the mixture stirred overnight. The mixture turned brown and a precipitate formed. The mixture was taken up in EtOAc (75 ml)/1N HCl (25 ml). It was filtered to remove the brown insoluble material. The layers were separated, and the EtOAc layer was washed with 1N HCl (25 ml), water (25 ml), 5% NaHCO₃ (25 ml), brine (10 ml), dried (MgSO₄), and evaporated to a yellow foam: 0.681 g.

The foam was taken up in 30 ml warm MeOH, stirred with 5 g charcoal for 15 min, filtered through Celite, and evaporated to a slightly colored oil: 0.55 g. The oil was triturated with 3 ml MeOH. Crystals formed immediately. After standing at 0° for 1 hour, the crystals were filtered, washed with cold MeOH (2×1 ml) and dried under vacuum overnight to give the title compound: 0.47 g (75%), mp. 117°-9°, [α]$_{D+14.5°}$ (c=1, CHCl₃).

Anal. calcd. for $C_{18}H_{17}NO_5$.0.1 H₂O (MW 327.32/329.2) C, 65.67; H, 5.27; N, 4.25; H₂O 0.57

Found: C, 65.75; H, 5.07; N, 4.43; H₂O 0.57 (KF)

C. [2(S) ,3aα,4β,7β,7aα]-Hexahydro-2-(2-hydroxy-1-phenylethyl)-4,7-epoxy-1H-isoindole -1,3(2H)-dione

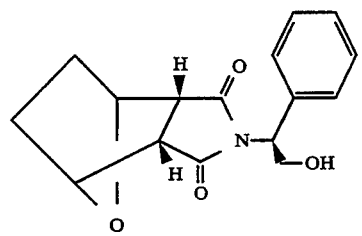

Part B compound (0.400 g, 1.22 mM) and 5% Pd/C (40 mg) were stirred in EtOAc (10 ml) and H₂ was sparged through the mixture for 1.2 hrs. TLC (silica gel, EtOAc/hexane 7:3 visualized with UV and KMnO₄)

showed the Part B olefin and the saturated intermediate

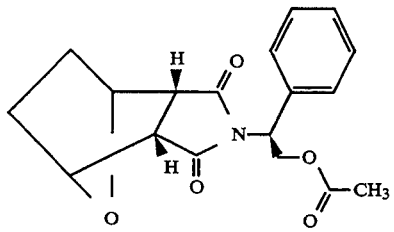

with the same $R_f$ 0.44. The olefin spot was KMnO$_4$ positive while the spot for the saturated intermediate (UV positive) from the reaction mixture was negative. N$_2$ was sparged through the mixture for 15 min to remove excess H$_2$. The catalyst was filtered through Celite and washed with EtOAc (4×2 ml). The filtrate was evaporated to an oil which solidified on standing after 2 days to saturated intermediate as fine white needles: 415 mg (quan. yield), mp. 96°–8°.

The above solid saturated intermediate (0.360 g, 1.06 mM) was dissolved in MeOH (10 ml) and K$_2$CO$_3$ (15 mg) was added and stirred for 4 hrs. The K$_2$CO$_3$ gradually dissolved. TLC (silica gel, EtOAc/hexane 7:3, visualized with UV and ceric ammonium molybdate) showed disappearance of saturated intermediate and appearance of a spot for the title compound at $R_f$0.20. MeOH was evaporated and the residue was taken up in EtOAc (25 ml) and washed with 1N HCl (10 ml), H$_2$O (10 ml), 5% NaHCO$_3$ (10 ml), and brine (10 ml), dried (MgSO$_4$), and evaporated: 0.29 g.

The residue was dissolved in hot EtOAc (1.5 ml) and hexane (3 ml) was added with heating. The solution was let stand at room temperature for 3 hrs and at 0° for 2 hrs. The crystals were filtered, washed with cold hexane, and dried under vacuum overnight to give the title compound as a white solid: 0.25 g (82%), mp 118°–9°, [α]$_D$ −16.0° (c=1.3, CHCl$_3$).

Anal. calcd. for C$_{16}$H$_{17}$NO$_4$, (MW 287.1) C, 66.89; H, 5.96; N, 4.88

Found: C, 66.83; H, 6.01; N, 5.06; H$_2$O 0.00 (KF)

D.
[2S-(2α,3aα,4β,7β,7aα)]-2-(Octahydro-3-oxo-4,7-epoxyisobenzofuran-1-yl)-benzaldehyde Following the procedure of Example 1 Parts C and D, the title benzaldehyde is obtained which is used in the procedure outlined in Example 6 to obtain the final product of Example 6.

Example 30A (S)-1-[2-(Acetyloxy)-1-phenylethyl]-2,5-dihydro-1H-pyrrol-2,5-dione (Alternative Synthesis)

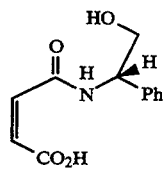

Maleic anhydride (358 mg, 3.65 mM) was added to (S)-(+)-2-phenylglycinol (500 mg, 3.65 mM) dissolved in 5 ml THF stirred under Ar. A precipitate formed immediately but redissolved after 1 hr. The mixture was stirred overnight. TLC (silica gel, EtOAc/HOAc 95:5) showed two spots, the product $R_f$0.34, and a lower Rf spot, $R_f$0.09. The THF was evaporated, and the residue was dissolved in 6 ml hot CH$_2$Cl$_2$. Crystals formed almost immediately in the hot mixture which was let stand at 5° for 2 hrs. The crystals were filtered, washed with cold CH$_2$Cl$_2$, and dried under vacuum to give the title compound: 600 mg (70%), mp. 131°–2°.

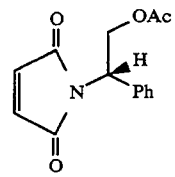

Acetic anhydride (5.38 ml, 57.1 mM) and triethylamine (7.94 ml, 57.1 mM) were added to the Part A amide acid (2.5 g, 11.4 mM) stirred in 20 ml THF. The mixture was refluxed in an 85° oil bath for 2.5 hrs (TLC: silica gel, EtOAc/HOAc 95:5, SM $R_f$0.34, product 0.71; the SM disappeared and an anhydride intermediate ($R_f$0.41) formed which disappeared into the product as the reaction proceeded). The mixture was allowed to cool to room temperature, 20 ml H$_2$O was added, and the mixture stirred for 1 hr to hydrolyze any anhydride. The mixture was taken up in 125 ml EtOAc, washed with 1N HCl (50 ml), H$_2$O (50 ml), 5% NaHCO$_3$ (50 ml), and brine (25 ml), and then dried (MgSO$_4$) and evaporated to give a black oil, 2.83 g.

The oil was chromatographed on silica gel (50×160 mm) eluted with 500 ml 10% EtOAc/Hexane and 500 ml 20% EtOAc/Hexane collecting 40 ml fractions. Pure fractions by TLC (silica gel, EtOAc/Hexane, 4:6, $R_f$0.37) were combined and evaporated to give the title compound in the form of a slightly colored oil: 2.01 g (69%).

Example 31

[1S-(1α,2α,3α,4α)]-2-[[3-[4-[(Pentylamino)carbonyl]-2-oxazolyl]-7-oxabicyclo[2.2.1]hept-2-yl]methyl]benzenepropanoic acid, magnesium (2:1) salt Example 6 compound (3.0 g, 6.82 mmol) was dissolved in 50 mL MeOH at 40° C. and the warm solution was poured into a mechanically stirred slurry of MgO (0.504 g, 12.5 mmol) in 50 mL water preheated at 40° C. under argon. MeOH (50 mL) was added to the reaction mixture. The pH of the suspension was 6. The temperature of the mixture was maintained at 40° C. The pH of the mixture rose to 9.5 over 15 min. The warm bath was removed and after stirring for 15 min. the mixture was filtered through a membrane filter (Rainin Nylon-66 filter 0.45 µm). The filter cake was washed with 15 mL mixture of MeOH/H$_2$O (2:1) and the solvent was evaporated on a rotary evaporator at 35° C. The product was redissolved in 15 mL MeOH and evaporated to dryness. The product was dried further under vacuum overnight to give 3.03 g (yield 97.4%) of the title magnesium salt, mp 142°–45° C., [α]$_D$=+8.1° (c=1, MeOH).

Analysis cald for (C$_{25}$H$_{31}$N$_2$O$_5$)$_2$ Mg.0.97 H$_2$O;

MW 903.38/920.81 C, 65.21; H, 7.00; N, 6.09; Mg, 2.64; H$_2$O, 1.90

Found: C, 65.07; H, 7.03; N, 5.92; Mg, 2.80; H$_2$O 1.90 (KF)

What is claimed is:

1. A method for preparing an alcohol-amide of the structure

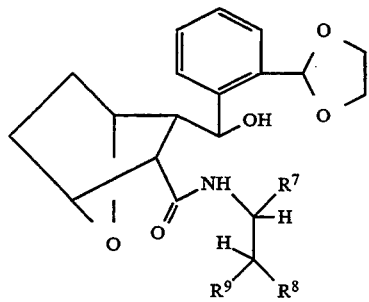

wherein R⁷ is aryl or lower alkyl,
R⁸ is H, aryl or lower alkyl, and
R⁹ is H, OH or lower alkyl, which comprises providing an imide of the structure

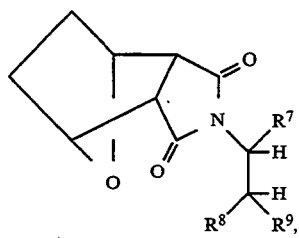

reacting the imide with a metallated aryl compound of the structure

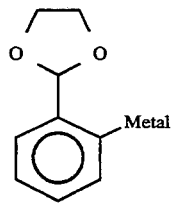

where Metal is MgBr or Li, to form a hemi-aminol of the structure

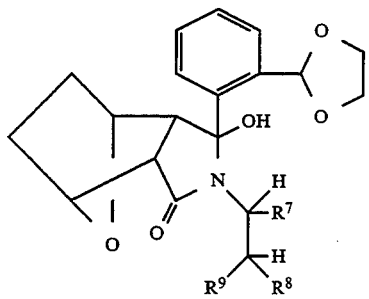

and reducing the above alcohol to form the alcohol-amide as defined above.

2. The method as defined in claim 1 wherein R⁹ is OH and the imide is reacted with an alkyl- or aryl magnesium halide and the Grignard reagent

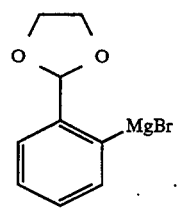

3. The method as defined in claim 1 wherein the imide is reacted with an alkyllithium compound R$^a$Li where R$^a$ is lower alkyl and an aryllithium compound

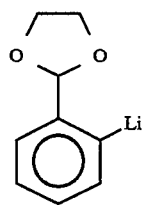

to form the hemi-aminol.

4. The method as defined in claim 1 wherein R⁷ is phenyl, R⁸ is H and R⁹ is OH or H.

* * * * *